United States Patent
Shields et al.

(10) Patent No.: US 10,632,189 B2
(45) Date of Patent: Apr. 28, 2020

(54) CANINE RESPIRATORY CORONAVIRUS FOR TREATMENT AND PROTECTION AGAINST BACTERIAL INFECTIONS

(71) Applicant: Zoetis Services LLC, Florham Park, NJ (US)

(72) Inventors: Shelly Lynn Shields, Kalamazoo, MI (US); Omar Yousif Abdelmagid, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 0 days.

(21) Appl. No.: 14/402,977

(22) PCT Filed: May 24, 2013

(86) PCT No.: PCT/US2013/042590
§ 371 (c)(1),
(2) Date: Nov. 21, 2014

(87) PCT Pub. No.: WO2013/181086
PCT Pub. Date: Dec. 5, 2013

(65) Prior Publication Data
US 2015/0157706 A1    Jun. 11, 2015

Related U.S. Application Data

(60) Provisional application No. 61/653,558, filed on May 31, 2012.

(51) Int. Cl.
| | |
|---|---|
| *A61K 39/215* | (2006.01) |
| *A61K 39/09* | (2006.01) |
| *A61K 39/12* | (2006.01) |
| *A61K 39/02* | (2006.01) |
| A61K 39/00 | (2006.01) |
| C12N 7/00 | (2006.01) |

(52) U.S. Cl.
CPC .......... *A61K 39/215* (2013.01); *A61K 39/099* (2013.01); *A61K 39/12* (2013.01); *A61K 2039/525* (2013.01); *A61K 2039/552* (2013.01); *A61K 2039/58* (2013.01); *C12N 7/00* (2013.01); *C12N 2770/20032* (2013.01); *C12N 2770/20034* (2013.01)

(58) Field of Classification Search
None
See application file for complete search history.

(56) References Cited

U.S. PATENT DOCUMENTS

| | | | |
|---|---|---|---|
| 2010/0028379 A1* | 2/2010 | Tucker et al. | 424/201.1 |
| 2013/0302369 A1* | 11/2013 | Abdelmagid et al. | 424/201.1 |
| 2014/0079733 A1* | 3/2014 | Abdelmagid et al. | 424/201.1 |

FOREIGN PATENT DOCUMENTS

| | | | |
|---|---|---|---|
| WO | 2004/011651 | | 2/2004 |
| WO | 2011/112593 | | 9/2011 |
| WO | WO 2012103821 | * | 8/2012 |
| WO | WO 2012104820 | * | 8/2012 |

OTHER PUBLICATIONS

Datz et al (Infectious Disease Compendium.vol. 25, No. 12, Dec. 2003 reterived online at http://www.vetfolio.com/infectious-disease/bordetella-infections-in-dogs-and-cats-pathogenesis-clinical-signs-and-diagnosis on Oct. 9, 2018.*
PCT International Search Report, PCT/US2013/042590, dated Aug. 26, 2013 (3 pages).

* cited by examiner

*Primary Examiner* — Oluwatosin A Ogunbiyi
(74) *Attorney, Agent, or Firm* — Vyacheslav Vasilyev

(57) ABSTRACT

Provided herein are compositions, combinations, and methods comprising Canine Respiratory Coronavirus (CRCoV), which are effective in treating or preventing respiratory infections associated secondary pathogens, such as *Bordetella bronchiseptica*, in animals.

6 Claims, No Drawings

CANINE RESPIRATORY CORONAVIRUS FOR TREATMENT AND PROTECTION AGAINST BACTERIAL INFECTIONS

This application is a 371 national filing of PCT/US2013/042590 filed May 24, 2013, now pending, which claims benefit of priority to U.S. Provisional Application Ser. No. 61/653,558 filed May 31, 2012.

FIELD OF THE INVENTION

The present invention relates to the field of immunology, and in particular to the field of immunogenic and vaccine compositions. More specifically, the present disclosure relates to compositions comprising Canine Respiratory Coronavirus (CRCoV) preparation for treatment or prevention of multi-factorial diseases, particularly comprising bacterial infections, in a dog.

BACKGROUND OF THE INVENTION

CRCoV is a highly contagious respiratory infection which is spread by direct dog-to-dog contact, aerosols of respiratory secretions, and contact with contaminated environments or people. Some dogs have a mild disease with symptoms consisting of cough, sneezing, and nasal discharge, while other dogs have a subclinical infection with no clinical signs, yet they shed virus that can infect other dogs. Dogs infected with CRCoV may progress to pneumonia, particularly if co-infected with other respiratory pathogens.

Dogs infected with multiple respiratory pathogens, particularly both viral and bacterial pathogens, may contract canine infectious respiratory disease complex (CIRDC), which is a highly contagious multifactorial disease common in dogs housed in crowded conditions, such as re-homing centers and boarding or training kennels. Respiratory pathogens seen in dogs infected with CIRD include the bacterium *Bordetella bronchiseptica* (Bemis et al., Lab. Anim. Sci., 29:48-52, 1977), canine respiratory coronavirus (CRCoV) (Erles et al., Virology, 310(2):216-223, 2003), canine influenza virus (CIV) (Crawford et al., Science, 310(5747):482-485, 2005), canine parainfluenzavirus (CPIV) (Binn et al., Exp. Biol. Med., 126:140-145, 1967), *Mycoplasma cynos* (Chalker et al., Microbiology, 150:3491-3497, 2004), and canine adenovirus serotype 2 (CAV-2) (Ditchfield et al., Can. Vet. J., 3:238-247, 1962). To date, no vaccine against all, or the majority, of the aforementioned pathogens has emerged.

Protection against CIRDC and other multi-pathogen diseases has traditionally focused on the administration of a combination vaccine that includes immunogens targeted against each of the potential pathogens.

SUMMARY OF THE INVENTION

The present invention surprisingly achieves what was previously sought in a multivalent product through the administration of only a single antigen. Specifically, by administering Canine Respiratory Coronavirus (CRCoV), applicants have shown reduction in disease state associated with non-CRCoV pathogens, namely *Bordetella bronchiseptica*. This allows both for reduction of a complex multi-faceted disease state with only a single monovalent composition and/or increase of immunogenicity and potentiation of efficacy against bacterial pathogens in a multivalent composition.

Accordingly, one aspect of the present invention provides a method of treating a bacterial disease in a dog, comprising administering a composition comprising canine respiratory coronavirus (CRCoV) to the dog. In a more particular embodiment, the bacterial disease is caused by at least one of: *Bordetella bronchiseptica, Mycoplasma cynos* (*M. cynos*) and *Streptococcus equi*., optionally subspecies *zooepidemicus*. In another embodiment, the composition further comprises a pharmaceutically acceptable carrier, diluent or excipient.

In another embodiment, the composition further comprises one or more additional immunogens. More particularly, the one or more additional immunogens are selected from the group consisting of canine parainfluenza virus (CPIV), canine adenovirus-2 (CAV-2), and canine influenza virus (CIV). In another embodiment, the one or more additional immunogens are selected from the group consisting of canine distemper virus (CDV), canine parvovirus (CPV), enteric canine coronavirus (CCV), canine adenovirus, *Leptospira* serovars, particularly, *Leptospira canicola, Leptospira grippotyphosa, Leptospira icterohaemorrhagiae, Leptospira pomona*, and *Leptospira Bratislava*, canine herpesvirus, canine pneumovirus, *Leishmania* organisms, a *Borrelia* species (spp.), *Mycoplasma* species, rabies, *Ehrlichia canis, Bordetella bronchiseptica* and any combination thereof. In another embodiment, the composition consists essentially of CRCoV and no additional immunogens.

In another embodiment, the composition has a duration of efficacy against the bacterial disease for a period of at least 3 months, or at least 6 months, or at least 12 months.

Another embodiment of the invention provides a method of protecting against canine respiratory disease in a dog caused by bacterial infections comprising administering canine respiratory coronavirus (CRCoV) to the dog.

Another embodiment of the invention provides a method of protecting against a multifactorial canine respiratory disease in a dog caused by mixed viral and bacterial infections comprising administering canine respiratory coronavirus (CRCoV) to the dog.

Another embodiment of the invention provides a method of treating a disease caused by *Bordetella bronchiseptica* in a dog, comprising administering a composition comprising canine respiratory coronavirus (CRCoV) to the dog.

Another embodiment of the invention provides a method of potentiating efficacy of a composition comprising a bacterial antigen in a dog, comprising co-administering canine respiratory coronavirus (CRCoV) to the dog. Another embodiment of the invention provides a method of increasing immunogenicity of a composition comprising a bacterial antigen in a dog, comprising co-administering canine respiratory coronavirus (CRCoV) to the dog. In a more particular embodiment of any of the foregoing, the bacterial antigen is from *Bordetella bronchiseptica*.

Another embodiment of the present invention provides a method or use of the immunogenic composition of any one of the foregoing embodiments for treatment or prevention of canine infectious respiratory disease complex (CIRDC), wherein the composition treats or prevents infection from a plurality of canine respiratory pathogens. Another embodiment provides for the use or method of parenterally administering an immunongenic composition as described herein.

Another embodiment provides for the manufacture of a medicament comprising the immunogenic composition for treatment or prevention of infection from a canine respiratory pathogen in a dog.

These and other embodiments, features, and advantages of the invention will become apparent from the detailed description and the appended claims set forth herein below. It is understood that each of the foregoing and following embodiments can be combined into a single embodiment.

DETAILED DESCRIPTION OF THE INVENTION

The definitions below apply to this disclosure. They supersede any contradictory definitions contained in each individual reference incorporated herein by reference. Words not defined have the meaning commonly used by one skilled in the art. Further, unless otherwise required by context, singular terms shall include pluralities and plural terms shall include the singular.

"About" or "approximately," when used in connection with a measurable numerical variable, refers to the indicated value of the variable and to all values of the variable that are within the experimental error of the indicated value (e.g., within the 95% confidence interval for the mean), or within 10 percent of the indicated value, whichever is greater. If "about" is used in reference to time intervals in weeks, "about 3 weeks" is 17 to 25 days, and "about 2 to about 4 weeks" is 10 to 40 days.

"Adjuvant", as used herein, refers to any substance which serves as a non-specific stimulator of the immune response. See below for a further description of adjuvants.

The term "animal", as used herein, includes any animal that is susceptible to infection from CRCoV and/or canine respiratory disease complex, including mammals, both domesticated and wild. Preferably, animal as used herein refers to a dog or a human.

"Antibody", as used herein, is any polypeptide comprising an antigen-binding site regardless of the source, method of production, or other characteristics. It refers to an immunoglobulin molecule or a fragment thereof that specifically binds to an antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions. An antibody that is "specific" for a given antigen indicates that the variable regions of the antibody recognize and bind a specific antigen exclusively. The term includes, but is not limited to: a polyclonal antibody, a monoclonal antibody, a monospecific antibody, polyspecific antibody, humanized antibody, a tetrameric antibody, a tetravalent antibody, a multispecific antibody, a single chain antibody, a domain-specific antibody, a single domain antibody, a domain-deleted antibody, a fusion protein, an ScFc fusion protein, a single-chain antibody, chimeric antibody, synthetic antibody, recombinant antibody, hybrid antibody, mutated antibody, and CDR-grafted antibodies. Antibodies can be intact immunoglobulins derived from natural sources or from recombinant sources, or can be immunoreactive portions of intact immunoglobulins. An "antibody" can be converted to an antigen-binding protein, which includes but is not limited to antibody fragments which include but are not limited to: Fab, F(ab')$_2$, an Fab' fragment, an Fv fragment, a single-chain Fv (ScFv) fragment, an Fd fragment, a dAb fragment, diabodies, a CDR3 peptide, a constrained FR3-CDR3-FR4 peptide, a nanobody, a bivalent nanobody, a small modular immunopharmaceutical (SMIPs), and a minibody and any of above mentioned fragments and their chemically or genetically manipulated counterparts, as well as other antibody fragments that retain antigen-binding function. Typically, such fragments would comprise an antigen-binding domain. As will be recognized by those of skill in the art, any of such molecules may be engineered (for example "germlined") to decrease its immunogenicity, increase its affinity, alter its specificity, or for other purposes.

"Antigen" or "immunogen", as used herein, refers to a molecule that contains one or more epitopes (linear, conformational or both) that upon exposure to a subject will induce an immune response that is specific for that antigen. An epitope is the specific site of the antigen which binds to a T-cell receptor or specific antibody, and typically comprises about 3 amino acid residues to about 20 amino acid residues. The term antigen refers to subunit antigens—antigens separate and discrete from a whole organism with which the antigen is associated in nature—as well as killed, attenuated or inactivated bacteria, viruses, fungi, parasites or other microbes. The term antigen also refers to antibodies, such as anti-idiotype antibodies or fragments thereof, and to synthetic peptide mimotopes that can mimic an antigen or antigenic determinant (epitope). The term antigen also refers to an oligonucleotide or polynucleotide that expresses an antigen or antigenic determinant in vivo, such as in DNA immunization applications.

"Antigenicity", as used herein, refers to the capability of a protein or polypeptide to be immunospecifically bound by an antibody raised against the protein or polypeptide.

The term "*Bordetella bronchiseptica*" or "*B. bronchiseptica*" refers to: a live attenuated bacterium of *Bordetella bronchiseptica*, a killed whole cell extract (bacterin) of *Bordetella bronchiseptica* or a cellular bacterial extract of *Bordetella bronchiseptica*.

The term "bacterial disease" or "bacterial infection" refers to a disease that is either cased directly by a particular bacteria (e.g. *B. bronchiseptica*) or exacerbated as a result the bacterial pathogen in a multifactorial disease state.

"Buffer" means a chemical system that prevents change in the concentration of another chemical substance. Proton donor and acceptor systems serve as buffers, preventing marked changes in hydrogen ion concentration (pH). A further example of a buffer is a solution containing a mixture of a weak acid and its salt (conjugate base), or a weak base and its salt (conjugate acid).

"Canine", as used herein, includes what is commonly called the dog, but includes other members of the family Canidae.

The term "cell line" or "host cell", as used herein, means a prokaryotic or eukaryotic cell in which a virus can replicate or be maintained.

The term co-administering refers to separate, sequential or simultaneous administration. Co-administered antigens or agents can be in the same composition, such as a multivalent combination vaccine or separate compositions comprising different dosage forms.

The term "culture", as used herein, means a population of cells or microorganisms growing in the absence of other species or types.

"Dose" refers to a vaccine or immunogenic composition given to a subject. A "first dose" or "priming dose" refers to the dose of such a composition given on Day 0. A "second dose" or a "third dose" or an "annual dose" refers to an amount of such composition given subsequent to the first dose, which can be but is not required to be the same vaccine or immunogenic composition as the first dose.

An "epitope" is the specific site of the antigen which binds to a T-cell receptor or specific antibody, and typically comprises from about 3 amino acid residues to about 20 amino acid residues.

"Excipient", as used herein, refers to a non-reactive carrier component of a vaccine or immunogenic composition that is not an antigen. Preferred excipients are those known in the art for parenteral injection.

"Fragment" refers to a truncated portion of a protein or gene. "Functional fragment" and "biologically active fragment" refer to a fragment that retains the biological properties of the full length protein or gene.

"Homology" or "percent homology" refers to the percentage of nucleotide or amino acid residues in the candidate sequence that are identical or similar with the residues in the comparator sequence(s) after aligning the sequences and introducing gaps, if necessary, to achieve the maximum percent sequence homology, and also considering any conservative substitutions as part of the sequence homology.

"Homologs" or "species homologs" include genes found in two or more different species which possess substantial polynucleotide sequence homology, and possess the same, or similar, biological functions and/or properties. Preferably polynucleotide sequences which represent species homologs will hybridize under moderately stringent conditions, as described herein by example, and possess the same or similar biological activities and/or properties. In another aspect, polynucleotides representing species homologs will share greater than about 60% sequence homology, greater than about 70% sequence homology, greater than about 80% sequence homology, greater than about 90% sequence homology, greater than about 95% sequence homology, greater than about 96% sequence homology, greater than about 97% sequence homology, greater than about 98% sequence homology, or greater than about 99% sequence homology.

"Identity" or "percent identity" refers to the percentage of nucleotides or amino acids in the candidate sequence that are identical with the residues in the comparator sequence after aligning both sequences and introducing gaps, if necessary, to achieve the maximum percent sequence identity, and not considering any conservative substitutions as part of the sequence identity.

"Immune response", as used herein, in a subject refers to the development of a humoral immune response, a cellular immune response, or a humoral and a cellular immune response to an antigen. A "humoral immune response" refers to one that is at least in part mediated by antibodies. A "cellular immune response" is one mediated by T-lymphocytes or other white blood cells or both, and includes the production of cytokines, chemokines and similar molecules produced by activated T-cells, white blood cells, or both. Immune responses can be determined using standard immunoassays and neutralization assays, which are known in the art.

"Immunogenicity", as used herein, refers to the capability of a protein or polypeptide to elicit an immune response directed specifically against a bacteria or virus that causes the identified disease.

An "immunogenic composition" is a preparation containing an immunogen, including, e.g., a protein, a peptide, a whole cell, inactivated, subunit or attenuated virus, or a polysaccharide, or combination thereof, administered to stimulate the recipient's humoral and cellular immune systems to one or more of the antigens present in the immunogenic composition. "Immunization" is the process of administering an immunogenic composition and stimulating an immune or immunogenic response to an antigen in a host. Preferred hosts are mammals, such as dogs. Preferably, the immunogenic composition is a vaccine.

"Immunologically protective amount", as used herein, is an amount of an antigen effective to induce an immunogenic response in the recipient that is adequate to prevent or ameliorate signs or symptoms of disease, including adverse health effects or complications thereof. Either humoral immunity or cell-mediated immunity or both can be induced. The immunogenic response of an animal to a composition can be evaluated, e.g., indirectly through measurement of antibody titers, lymphocyte proliferation assays, or directly through monitoring signs and symptoms after challenge with wild type strain. The protective immunity conferred by a composition or vaccine can be evaluated by measuring, e.g., reduction of shed of challenge organisms, reduction in clinical signs such as mortality, morbidity, temperature, and overall physical condition, health and performance of the subject, reduction of pathology, gross and histopathology in vital tissues. The immune response can comprise, without limitation, induction of cellular and/or humoral immunity. The amount of a composition or vaccine that is therapeutically effective can vary, depending on the particular organism used, or the condition of the animal being treated or vaccinated, and can be determined by a veterinarian.

"Intranasal" administration, as used herein, refers to the introduction of a substance, such as a vaccine or other composition, into a subject's body through or by way of the nose, and involves transport of the substance primarily through the nasal mucosa.

The term "isolated" refers to a substance that is either in substantially pure form, for example, greater than about 95% purity; or purified or enriched in some way from its natural environment. The term "isolated" encompasses immunogens that are in solution with other agents/diluents/excipients/adjuvants/proteins.

"Medicinal agent" refers to any agent which is useful in the prevention, cure, or improvement of a medical condition, or the prevention of some physiological condition or occurrence.

"Monoclonal antibody", as used herein, refers to antibodies produced by a single line of hybridoma cells, all directed towards one epitope on a particular antigen. The antigen used to make the monoclonal antibody can be provided as an isolated protein of the pathogen or the whole pathogen. A "hybridoma" is a clonal cell line that consists of hybrid cells formed by the fusion of a myeloma cell and a specific antibody-producing cell. In general, monoclonal antibodies are of mouse origin. However, monoclonal antibody also refers to a clonal population of an antibody made against a particular epitope of an antigen produced by phage display technology, or method that is equivalent to phage display, or hybrid cells of non-mouse origin.

"Oral" or "peroral" administration, as used herein, refers to the introduction of a substance, such as a vaccine or other composition, into a subject's body through or by way of the mouth and involves swallowing or transport through the oral mucosa (e.g., sublingual or buccal absorption) or both. Intratracheal is also a means of oral or peroral administration.

"Oronasal" administration, as used herein, refers to the introduction of a substance, such as a composition or vaccine, into a subject's body through or by way of the nose and the mouth, as would occur, for example, by placing one or more droplets in the nose. Oronasal administration involves transport processes associated with oral and intranasal administration.

"Parenteral administration", as used herein, refers to the introduction of a substance, such as a composition or vaccine, into a subject's body through or by way of a route that does not include the digestive tract. Parenteral administration includes subcutaneous, intramuscular, intraarterial, and intravenous administration. For the purposes of this disclosure, parenteral administration excludes administration routes that primarily involve transport of the substance through mucosal tissue in the mouth, nose, trachea, and lungs.

The term "pathogen" or "pathogenic microorganism", as used herein, means a microorganism—for example CPIV, CAV-2, CRCoV, *Mycoplasma cynos*, CIV, or *Bordetella bronchiseptica*—which is capable of inducing or causing a disease, illness, or abnormal state in its host animal, preferably a respiratory disease, such as CIRDC.

"Pharmaceutically acceptable" refers to substances which, within the scope of sound medical judgment, are suitable for use in contact with the tissues of subjects without undue toxicity, irritation, allergic response, and the like, commensurate with a reasonable benefit-to-risk ratio, and effective for their intended use.

"Polyclonal antibody", as used herein, refers to a mixed population of antibodies made against a particular pathogen or antigen. In general, the population contains a variety of antibody groups, each group directed towards a particular epitope of the pathogen or antigen. To make polyclonal antibodies, the whole pathogen, or an isolated antigen, is introduced by inoculation or infection into a host, which induces the host to make antibodies against the pathogen or antigen.

The term "polynucleotide", as used herein, means an organic polymer molecule composed of nucleotide monomers covalently bonded in a chain. DNA (deoxyribonucleic acid) and RNA (ribonucleic acid) are examples of polynucleotides with distinct biological function.

The term "polypeptide", as used herein, means an organic polymer molecule composed of two or more amino acids bonded in a chain.

"Respiratory" administration, as used herein, refers to the introduction of a substance, such as a vaccine or other composition, into a subject's body through or by way of inhalation of a nebulized (atomized) substance. In respiratory administration, the primary transport mechanism involves absorption of the atomized substance through the mucosa in the trachea, bronchi, and lungs and is therefore different than intranasal or peroral administration.

The terms "specific binding," "specifically binds," and the like, are defined as two or more molecules that form a complex that is measurable under physiologic or assay conditions and is selective. An antibody or other inhibitor is said to "specifically bind" to a protein if, under appropriately selected conditions, such binding is not substantially inhibited, while at the same time non-specific binding is inhibited. Specific binding is characterized by high affinity and is selective for the compound or protein. Nonspecific binding usually has low affinity. Binding in IgG antibodies, for example, is generally characterized by an affinity of at least about $10^{-7}$ M or higher, such as at least about $10^{-8}$ M or higher, or at least about $10^{-9}$ M or higher, or at least about $10^{-10}$ or higher, or at least about $10^{-11}$ M or higher, or at least about $10^{-12}$ M or higher. The term is also applicable where, e.g., an antigen-binding domain is specific for a particular epitope that is not carried by numerous antigens, in which case the antibody carrying the antigen-binding domain will generally not bind other antigens.

"Specific immunogenic fragment", as used herein, refers to a portion of a sequence that is recognizable by an antibody or T cell specific for that sequence.

"Subject", as used herein, refers to any animal having an immune system, which includes mammals, such as dogs.

"Substantially identical", as used herein, refers to a degree of sequence identity of at least about 90%, at least about 95%, at least about 96%, at least about 97%, at least about 98%, or at least about 99%.

"Subunit vaccine", and "subunit composition", as used herein, refers to a type of vaccine or composition that includes an antigens—but not all antigens—which are derived from or homologous to, antigens from a pathogen of interest, such as a virus, bacterium, parasite or fungus. Such a composition or vaccine is substantially free of intact pathogen cells or pathogenic particles, or the lysate of such cells or particles. Thus, a subunit vaccine or subunit composition can be prepared from at least partially purified, or substantially purified, immunogenic polypeptides from the pathogen or their analogs. Methods of obtaining an antigen or antigens in the subunit vaccine or subunit composition include standard purification techniques, recombinant production, or chemical synthesis. A "subunit vaccine" or "subunit composition" thus refers to a vaccine or composition consisting of a defined antigenic component or components of a virus, bacterium, or other immunogen.

"$TCID_{50}$" refers to "tissue culture infective dose" and is defined as that dilution of a virus required to infect 50% of a given batch of inoculated cell cultures. Various methods can be used to calculate $TCID_{50}$, including the Spearman-Karber method, which is utilized throughout this specification. For a description of the Spearman-Karber method, see B. W. Mahy & H. O. Kangro, *Virology Methods Manual* 25-46 (1996).

"Therapeutic agent", as used herein, refers to any molecule, compound, virus or treatment, preferably a virus attenuated or killed, or subunit or compound, that assists in the treatment of a viral, bacterial, parasitic or fungal infection, disease or condition caused thereby.

"Therapeutically effective amount", as used herein, refers to an amount of an antigen or vaccine or composition that would induce an immune response in a subject (e.g., dog) receiving the antigen or vaccine or composition which is adequate to prevent or ameliorate signs or symptoms of disease, including adverse health effects or complications thereof, caused by infection with a pathogen, such as a virus, bacterium, parasite or fungus. Humoral immunity or cell-mediated immunity, or both humoral and cell-mediated immunity, can be induced. The immunogenic response of an animal to an antigen, vaccine, or composition can be evaluated indirectly through measurement of antibody titers, lymphocyte proliferation assays, or directly through monitoring signs and symptoms after challenge with the wild type strain. The protective immunity conferred by a vaccine or composition can be evaluated by measuring reduction of challenge organism shed, and/or reduction in clinical signs, such as mortality, morbidity, temperature, and overall physical condition, health, and performance of the subject. The amount of a vaccine or composition that is therapeutically effective can vary, depending on the particular immunogen used, or the condition of the subject, and can be determined by one skilled in the art.

"Treating" or "treatment" of a disease in a patient refers to: inhibiting the disease or arresting its development; protecting against the disease or preventing the disease from occurring in a patient that is predisposed or does not yet display symptoms of the disease; or ameliorating or causing regression of the disease. Likewise, the terms, "protect," "protecting," "protection" and the like mean the reduction or elimination of clinical signs of disease. It can also mean the reduction or elimination of the causative agent(s) of disease.

"Vaccine" or "vaccine composition," as used herein, refers to an immunogenic composition selected from a virus or bacteria, either modified live, attenuated, or killed, or a subunit vaccine, or any combination of the aforementioned. Administration of the vaccine to a subject results in an immune response. The vaccine can be introduced directly into the subject by any known route of administration, including parenterally, perorally, and the like. The terms mean a composition which prevents or reduces an infection, or which prevents or reduces one or more signs or symptoms of infection. The protective effects of a vaccine composition against a pathogen are normally achieved by inducing in the subject an immune response. Generally speaking, abolished or reduced incidences of infection, amelioration of the signs or symptoms, or accelerated elimination of the microorganism from the infected subjects are indicative of the protective effects of a vaccine composition. The vaccine compositions of the present invention provide protective effects against infections caused by canine respiratory disease pathogens.

"Veterinarily acceptable", as used herein, refers to substances which are, within the scope of sound medical judgment, suitable for use in contact with the tissues of veterinary subjects without undue toxicity, irritation, allergic response, and the like, commensurate with a reasonable benefit-to-risk ratio, and effective for their intended use.

"Veterinarily acceptable carrier", as used herein, refers to a carrier medium that does not interfere with the effectiveness of the biological activity of the active ingredient, and is not toxic to the veterinary subject to whom it is administered.

Antigens, Immunogenic Compositions, and Vaccines

The present invention provides immunogenic compositions and vaccines comprising one or more viruses, particularly CRCoV and optionally bacteria or subunits that are suitable for administration to a canine for treatment against a disease, such as CIRDC. The canine respiratory coronavirus (CRCoV) encompassed by this invention can be characterized as a coronavirus present in the respiratory tracts of dogs with infectious respiratory disease. CRCoV is phylogenetically most closely related to bovine coronavirus (BCoV), human coronavirus (HCoV) strain OC43 and hemagglutinating encephalomyelitis virus (HEV); enteric canine coronavirus (CCoV) is only distantly related to CRCoV.

In a preferred embodiment, the CRCoV is the same as that described in US 2007-0098739, the contents of which are hereby incorporated by reference, in particular with respect to the CRCoV strains and antigens described therein. Suitable immunogenic fragments of CRCoV are described in WO 2004/011651 (The Royal Veterinary College). Suitable immunogenic fragments of CRCoV include the Spike (S) and the hemagglutinin-esterase (HE) surface proteins, the membrane glycoprotein (M), and the nucleocapsid protein (N), or immunogenic portions thereof. The CRCoV-like Spike and HE proteins described in WO 2004/011651 may also be suitable as agents that raise an immune response against CRCV. Closely related coronaviruses, such as bovine coronavirus and human coronavirus, and immunogenic fragments thereof, may also be suitable as agents that raise an immune response against CRCV. The entire disclosure of WO 2004/011651 relating to agents that can be used as a vaccine component against CRCV is incorporated herein by reference. Another example of a CRCoV suitable for use in the present invention includes a strain identified as CRCoV strain 4182 (Erles et al., Virus Res., 124:78-87, 2007).

The influenza virus antigens encompassed by this invention can be any identified influenza virus strain, from any bird or mammal, including but not limited to, influenza virus having the subtype H3 hemagglutinin and subtype N8 neuraminidase, or the H3N8 subtype, more commonly referred to as an H3N8 virus. The influenza can be of mammalian or avian origin, including but not limited to swine, equine or canine origin. In one embodiment a canine influenza antigen is used. In one embodiment an equine influenza antigen is used. In one embodiment, a strain having the subtype glycoproteins designated H3 or N8 is used. In one embodiment, a strain having both subtype H3 and N8 glycoproteins is used.

The influenza antigens encompassed by this invention can be isolated from dogs, horses, pigs, and fowl, both domestic and wild. The animals chosen for sample collection should display acute and/or sub-acute clinical syndromes, which can include mild to severe respiratory symptoms and fever. Animals can also exhibit signs of anorexia and lethargy. Methods of virus isolation are well known to those skilled in the art including: inoculating mammalian or avian cell cultures, inoculating embryonated eggs with nasal or pharyngeal mucus samples from clinical specimens, collection by swabbing of the nasal passage or throat, or by collecting tissues such as spleen, lung, tonsil and liver and lung lavage. The cytopathic effect of the virus can be observed in cell culture. Allantoic fluid or cell lysates can be tested for their ability to agglutinate human, chicken, turkey or guinea pig red blood cells, presumptive evidence for the presence of an influenza virus.

A representative example of a canine influenza virus (CIV) strain suitable for use in the present invention includes a strain identified as A/canine/Iowa/9A1/B5/08/D12, which was deposited as PTA-7694 on 29 Jun. 2006 at the American Type Culture Collection (ATCC), 10801 University Boulevard, Manassas, Va. 20110-2209. A representative strain of the CIV antigen is the CIV virus strain in the commercial vaccine, Vanguard® CIV (Pfizer). This invention also encompasses vaccines comprising a strain identified as Equine Influenza Strain A/Equine/2/Miami/1/63. This strain is deposited at the ATCC, with accession number VR 317. Additional examples of influenza viruses for use in the present invention are A/canine/Iowa/13628/2005, A/Equine/Kentucky/1998, A/Equine/Kentucky/15/2002, A/Equine/Ohio/1/2003, A/Equine/Kentucky/1/1994, A/Equine/Massachusetts/213/2003, A/Equine/Wisconsin/2003, A/Equine/NewYork/1999, and A/Equine/Newmarket/A2/1993. Other preferred strains and/or isolates of CIV include those disclosed in U.S. Pat. No. 7,959,929 (particularly strains and HA sequences identified therein as Jacksonville/2005, Miami/2005, FL/242/03 and Florida/43/04), U.S. Pat. Nos. 7,384,642, 7,572,620 and 7,468,187, the contents of which, including all sequences, particularly HA sequences, and strains, are hereby incorporated by reference as if set forth fully herein. Additionally, a CIV strain suitable for use herein includes the Colorado CIV isolate described in Barrell et al., J. Vet. Intern. Med., 24 (6), 1524-1527 (2010), having accession number ADW41784.

The canine parainfluenza virus (CPIV) encompassed by this invention can be characterized as one of the viruses known to be a causative agent associated with kennel cough. A representative strain of the CPIV antigen is the attenuated CPI virus strain in the commercial vaccine, Vanguard® Plus 5 (Pfizer). Another representative strain of the CPIV antigen is the attenuated CPI virus strain having the designation of "NL-CPI-5" (National Veterinary Service Laboratory, Ames, Iowa).

The canine adenovirus, type 2 (CAV-2) encompassed by this invention can be characterized as one of the viruses also known to be a causative agent associated with kennel cough. A representative strain of the CAV-2 antigen is the attenuated CAV-2 virus strain in the commercial vaccine, Vanguard® Plus 5 (Pfizer). A representative strain of the CAV-2 antigen is the attenuated CAV-2 strain designated as the "Manhattan" strain (National Veterinary Service Laboratory, Ames, Iowa).

The *Mycoplasma cynos* (*M. cynos*) encompassed by this invention is described in Chalker et al., Microbiology, 150:3491-3497, 2004 and is the only species of mycoplasma commonly associated with respiratory disease. Immunogenic compositions against *M. cynos* are described in US 2007/0098739, incorporated herein by reference.

The *Bordetella bronchiseptica* component encompassed by this invention can be characterized as the bacterial causative agent associated with kennel cough. The immunogenic compositions and vaccines encompassed by the present invention can be one or more of: a live attenuated *Bordetella bronchiseptica*, a *Bordetella bronchiseptica* bacterin or a bacterial extract. Additionally, the composition preferably also includes an isolated subunit antigen of *Bordetella bronchiseptica*.

In one embodiment the *Bordetella bronchiseptica* is prepared as a whole cell sonicate purified through column chromatography as provided in Patent Application No. FR2571618, filed Oct. 12, 1984. Another representative example of a *Bordetella bronchiseptica* is the bacterial extract Bronchicine™ CAe (Pfizer), which is prepared from antigenic material extracted from *Bordetella bronchiseptica* cells. Another example of *Bordetella bronchiseptica* is the live attenuated *bronchiseptica* strain B-C2 present in Nobivac® and/or the live *bronchiseptica* strain from Intra-Trac®, Bronchi-Shield®, Naramune™, Recombitek®, Univac, and/or Kennel-Jec™.

Additionally, a subunit may also present (i.e. supplemented), in combination with the *Bordetella bronchiseptica* component. A representative example of the subunit is an isolated pertactin antigen, preferably, a *Bordetella bronchiseptica* p68 antigen, particularly the recombinant *Bordetella bronchiseptica* p68 antigen which is recognized by the p68-specific monoclonal antibody Bord 2-7 (described in U.S. Pat. No. 7,736,658, incorporated herein by reference) and in one preferred embodiment, has an amino acid sequence as set forth in U.S. Pat. No. 7,736,658 or having homology thereto.

Viruses encompassed by the present invention can be propagated in cells, cell lines and host cells. Said cells, cell lines or host cells can be for example, but not limited to, mammalian cells and non-mammalian cells, including insect and plant cells. Cells, cell lines, and host cells in which viruses encompassed by the present invention can be propagated are readily known, and accessible to those of ordinary skill in the art.

Bacteria encompassed by the present invention can be cultured and propagated using various culture media known to those of ordinary skill in the art, including both broth (liquid) and agar (solid; semi-solid) cultivation media. Some bacteria can also be cultured and propagated in mammalian cells or non-mammalian cells.

The viruses and bacteria encompassed by the present invention can be attenuated or inactivated prior to use in an immunogenic composition or vaccine. Methods of attenuation and inactivation are well known to those skilled in the art. Methods for attenuation include, but are not limited to, serial passage in cell culture on a suitable cell line (viruses and some bacteria), serial passage in broth culture (bacteria), ultraviolet irradiation (viruses and bacteria), and chemical mutagenesis (viruses and bacteria). Methods for viral or bacterial inactivation include, but are not limited to, treatment with formalin, betapropriolactone (BPL) or binary ethyleneimine (BEI), or other methods known to those skilled in the art.

Inactivation by formalin can be performed by mixing the suspension containing the microorganism with 37% formaldehyde to a final formaldehyde concentration of 0.5%. The microorganism-formaldehyde mixture is mixed by constant stirring for approximately 24 hours at room temperature. The inactivated microorganism mixture is then tested for residual live organisms by assaying for growth on a suitable cell line or broth media.

For some antigens, inactivation by BEI can be performed by mixing the suspension containing the microorganism of the present invention with 0.1 M BEI (2-bromo-ethylamine in 0.175 N NaOH) to a final BEI concentration of 1 mM. For other antigens, the final BEI concentration is 2 mM. One skilled in the art would know the appropriate concentration to use. The virus-BEI mixture is mixed by constant stirring for approximately 48 hours at room temperature, followed by the addition of 1.0 M sodium thiosulfate to a final concentration of 0.1 mM. Mixing is continued for an additional two hours. The mixture containing the inactivated microorganism is tested for residual live virus by assaying for growth on a suitable cell line or broth media.

Immunogenic compositions and vaccines encompassed by the present invention can include one or more veterinarily-acceptable carriers. As used herein, a "veterinarily-acceptable carrier" includes any and all solvents, dispersion media, coatings, adjuvants, stabilizing agents, diluents, preservatives, antibacterial and antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others known to those skilled in the art. Stabilizers include albumin, among others known to the skilled artisan. Preservatives include merthiolate, among others known to the skilled artisan.

The adjuvant can be metabolizable, referring to adjuvants consisting of components that are capable of being metabolized by the target species such as vegetable oil based adjuvants. A metabolizable adjuvant can be a metabolizable oil. Metabolizable oils are fats and oils that typically occur in plants and animals, and usually consist largely of mixtures of triacylglycerols, also known as triglycerides or neutral fats. These nonpolar, water insoluble substances are fatty acid triesters of glycerol. Triacylglycerols differ according to the identity and placement of their three fatty acid residues or side chains.

The adjuvant can also be non-metabolizable, referring to adjuvants consisting of components that cannot be metabolized by the body of the animal subject to which the emulsion is administered. Non-metabolizable oils suitable for use in compositions of the present invention include alkanes, alkenes, alkynes, and their corresponding acids and alcohols, the ethers and esters thereof, and mixtures thereof. Preferably, the individual compounds of the oil are light hydrocarbon compounds, i.e., such components have 6 to 30 carbon atoms. The oil can be synthetically prepared or purified from petroleum products. Preferred non-metabolizable oils for use in compositions described herein include mineral oil, paraffin oil, and cycloparaffins, for example. The term "mineral oil" refers to a non-metabolizable adjuvant oil that is a mixture of liquid hydrocarbons obtained from petrolatum via a distillation technique. The term is synonymous with "liquefied paraffin", "liquid petrolatum" and "white mineral oil." The term is also intended to include "light mineral oil," i.e., oil which is similarly obtained by distillation of petrolatum, but which has a slightly lower specific gravity than white mineral oil. Mineral oil can be obtained from various commercial sources, for example, J. T. Baker (Phillipsburg, Pa.), USB Corporation (Cleveland, Ohio). Light mineral oil is commercially available under the name DRAKEOL®.

Adjuvants include, but are not limited to, the Emulsigen adjuvant system (MVP Laboratories; Ralston, Nebr.), the RIBI adjuvant system (Ribi Inc.; Hamilton, Mont.), alum, aluminum hydroxide gel, oil-in water emulsions, water-in-oil emulsions such as, e.g., Freund's complete and incomplete adjuvants, Block copolymer (CytRx; Atlanta, Ga.), SAF-M (Chiron; Emeryville, Calif.), AMPHIGEN® adjuvant, saponin, Quil A, QS-21 (Cambridge Biotech Inc.; Cambridge, Mass.), GPI-0100 (Galenica Pharmaceuticals, Inc.; Birmingham, Ala.) or other saponin fractions, monophosphoryl lipid A, Avridine lipid-amine adjuvant, heat-labile enterotoxin from *E. coli* (recombinant or otherwise), cholera toxin, muramyl dipeptide, squalene/pluronic block copolymer/surfactant (SP-oil), sulpholipobeta-cyclodextrin (SL-CD), liposomes containing an immumodulator (e.g., CpG or poly I:C), muramyl dipeptide (MDP), iscomatrix (Quil A/phosphotidyl choline), CpG/DEAE-dextran/mineral oil (TXO), CpG, triterpenoids (e.g., Quil A or another purified or partially purified saponin preparation), sterols (e.g., cholesterol), immunomodulatory agents (e.g., dimethyl dioctadecyl ammonium bromide—DDA), polymers (e.g., polyacrylic acid such as CARBOPOL®), and Th2 stimulants (e.g., glycolipids such as Bay R1005®), and combinations thereof, among many other adjuvants known to those skilled in the art.

Non-limiting examples of various combinations that can be used include a is triterpenoid plus a sterol (e.g., Quil A/cholesterol, also known as QAC), a triterpenoid plus a sterol, an immunomodulatory agent, and a polymer (e.g., Quil A/cholesterol/DDA/CARBOPOL®, also known as QCDC), and a triterpenoid plus a sterol, an immunomodulatory agent, a polymer, and a Th2 stimulant (e.g., Quil A/cholesterol/DDA/CARBOPOL®, and Bay R1005®, also known as QCDCR).

The amounts and concentrations of adjuvants and additives useful in the context of the present invention can readily be determined by the skilled artisan. In one embodiment, the present invention contemplates immunogenic compositions and vaccines comprising from about 20 µg to about 2000 µg of adjuvant. In another embodiment, adjuvant is included in an amount from about 100 µg to about 1500 µg, or from about 250 µg to about 1000 µg, or from about 350 µg to about 750 µg. In another embodiment, adjuvant is included in an amount of about 500 µg/2 ml dose of the immunogenic composition or vaccine.

The immunogenic compositions and vaccines can also include antibiotics. Such antibiotics include, but are not limited to, those from the classes of aminoglycosides, carbapenems, cephalosporins, glycopeptides, macrolides, penicillins, polypeptides, quinolones, sulfonamides, and tetracyclines. In one embodiment, the present invention contemplates immunogenic compositions and vaccines comprising from about 1 µg/ml to about 60 µg/ml of antibiotic. In another embodiment, the immunogenic compositions and vaccines comprise from about 5 µg/ml to about 55 µg/ml of antibiotic, or from about 10 µg/ml to about 50 µg/ml of antibiotic, or from about 15 µg/ml to about 45 µg/ml of antibiotic, or from about 20 µg/ml to about 40 µg/ml of antibiotic, or from about 25 µg/ml to about 35 µg/ml of antibiotic. In yet another embodiment, the immunogenic compositions and vaccines comprise less than about 30 µg/ml of antibiotic.

Immunogenic compositions and vaccines encompassed by the present invention can include one or more polynucleotide molecules encoding for a virus or bacteria, or viral or bacterial protein. DNA or RNA molecules can be used in immunogenic compositions or vaccines. The DNA or RNA molecule can be administered absent other agents, or it can be administered together with an agent facilitating cellular uptake (e.g., liposomes or cationic lipids). Total polynucleotide in the immunogenic composition or vaccine will generally be between about 0.1 µg/ml and about 5.0 mg/ml. In another embodiment, the total polynucleotide in the immunogenic composition or vaccine will be from about 1 µg/ml and about 4.0 mg/ml, or from about 10 µg/ml and about 3.0 mg/ml, or from about 100 µg/ml and about 2.0 mg/ml. Vaccines and vaccination procedures that utilize nucleic acids (DNA or mRNA) have been well described in the art, for example, U.S. Pat. Nos. 5,703,055, 5,580,859, 5,589,466, all of which are incorporated herein by reference.

In addition to the viruses or bacteria described above, immunogenic compositions and vaccines encompassed by the present invention can include other additional antigens. Antigens can be in the form of an inactivated whole or partial preparation of the microorganism, or in the form of antigenic molecules obtained by genetic engineering techniques or chemical synthesis. Other antigens appropriate for use in accordance with the present invention include, but are not limited to, those derived from pathogenic viruses such as canine distemper virus, canine herpesvirus, canine influenza virus, rabies virus, pathogenic bacteria such as *Leptospira bratislava*, *Leptospira canicola*, *Leptospira grippotyphosa*, *Leptospira icterohaemorrhagiae*, *Leptospira pomona*, *Leptospira hardjobovis*, *Porphyromonas* spp., *Bacteriodes* spp., *Borrelia* spp., *Streptococcus* spp., including *Streptococcus equi* subspecies *zooepidemicus*, *Ehrlichia* spp., *Mycoplasma* spp., including *Mycoplasma cynos*, and *Microsporum canis*. Antigens can also be derived from pathogenic fungi such as *Candida*, protozoa such as *Cryptosporidium parvum*, *Neospora caninum*, *Toxoplasma gondii*, *Eimeria* spp., *Babesia* spp., *Giardia* spp., *Leishmania* spp., or helminths such as *Taenia*, *Cuterebra*, *Echinococcus*, and *Paragonimus* spp.

Forms, Dosages, Routes of Administration

Immunogenic compositions and vaccines encompassed by the present invention can be administered to animals to induce an effective immune response against multi-pathogenic disease states associated with CRCoV and another pathogen, such as *B. bronchiseptica*. Accordingly, the present invention provides methods of stimulating an effective immune response by administering to an animal a therapeutically effective amount of an immunogenic composition or vaccine described herein.

Immunogenic compositions and vaccines described herein can be administered to an animal to vaccinate the animal subject against CIRDC. The immunogenic compositions and vaccines can be administered to the animal to prevent or treat CIRDC in the animal. Accordingly, described herein are methods of vaccinating an animal against CIRDC, and preventing or treating CIRDC, comprising administering to the animal a therapeutically effective amount of an immunogenic composition or vaccine described herein.

Immunogenic compositions and vaccines encompassed by the present invention can be made in various forms depending upon the route of administration. For example, the immunogenic compositions and vaccines can be made in the form of sterile aqueous solutions or dispersions suitable for injectable use, or made in lyophilized forms using freeze-drying techniques. Lyophilized immunogenic compositions and vaccines are typically maintained at about 4° C., and can be reconstituted in a stabilizing solution, e.g., saline or HEPES, with or without adjuvant. Immunogenic compositions and vaccines can also be made in the form of suspensions or emulsions.

Immunogenic compositions and vaccines of the present invention include a therapeutically effective amount of one or more of the above-described microorganisms. Purified viruses and/or bacteria can be used directly in an immunogenic composition or vaccine, or can be further attenuated, or inactivated. Typically, an immunogenic composition or vaccine contains between about $1 \times 10^2$ and about $1 \times 10^{12}$ viral or bacterial particles, or between about $1 \times 10^3$ and about $1 \times 10^{11}$ particles, or between about $1 \times 10^4$ and about $1 \times 10^{10}$ particles, or between about $1 \times 10^5$ and about $1 \times 10^9$ particles, or between about $1 \times 10^6$ and about $1 \times 10^8$ particles. The precise amount of a microorganism in an immunogenic composition or vaccine effective to provide a protective effect can be determined by a skilled artisan.

The immunogenic compositions and vaccines generally comprise a veterinarily-acceptable carrier, in a volume of between about 0.5 ml and about 5 ml. In another embodiment the volume of the carrier is between about 1 ml and about 4 ml, or between about 2 ml and about 3 ml. In another embodiment, the volume of the carrier is about 1 ml, or is about 2 ml, or is about 5 ml. Veterinarily-acceptable carriers suitable for use in immunogenic compositions and vaccines can be any of those described hereinabove.

Those skilled in the art can readily determine whether a virus or bacteria needs to be attenuated or inactivated before administration. In another embodiment of the present invention, a virus or bacterium can be administered directly to an animal without additional attenuation. The amount of a microorganism that is therapeutically effective can vary, depending on the particular microorganism used, the condition of the animal and/or the degree of infection, and can be determined by a skilled artisan.

In accordance with the methods of the present invention, a single dose can be administered to animals, or, alternatively, two or more inoculations can take place with intervals of from about two to about ten weeks. Boosting regimens can be required, and the dosage regimen can be adjusted to provide optimal immunization. Those skilled in the art can readily determine the optimal administration regimen.

Immunogenic compositions and vaccines can be administered directly into the bloodstream, into muscle, into an internal organ, or under the skin. Suitable means for parenteral administration include intravenous, intraarterial, intramuscular, and subcutaneous administration. Suitable devices for parenteral administration include needle (including microneedle) injectors and needle-free injectors.

Parenteral formulations are typically aqueous solutions which can contain excipients such as salts, carbohydrates, proteins, and buffering agents (preferably to a pH of from about 3 to about 9, or from about 4 to about 8, or from about 5 to about 7.5, or from about 6 to about 7.5, or 7 to about 7.5), but, for some applications, they can be more suitably formulated as a sterile non-aqueous solution or as a dried form to be used in conjunction with a suitable vehicle such as sterile, pyrogen-free water or saline.

The preparation of parenteral formulations under sterile conditions, for example, by lyophilization, can readily be accomplished using standard pharmaceutical techniques well known to those skilled in the art.

The solubility of materials used in the preparation of parenteral solutions can be increased by the use of appropriate formulation techniques known to the skilled artisan, such as the incorporation of solubility-enhancing agents, including buffers, salts, surfactants, liposomes, cyclodextrins, and the like.

Compositions for parenteral administration can be formulated to be immediate or modified release. Modified release formulations include delayed, sustained, pulsed, controlled, targeted and programmed release. Thus, immunogenic compositions and vaccines can be formulated as a solid, semi-solid, or thixotropic liquid for administration as an implanted depot, providing modified release of the immunogenic compositions and vaccines.

Other means of immunogenic composition or vaccine administration include delivery by microneedle or needle-free (e.g. Powderject™, Bioject™, etc.) injection.

In cases where subcutaneous or intramuscular injection is used, an isotonic formulation is preferred. Generally, additives for isotonicity can include sodium chloride, dextrose, mannitol, sorbitol, and lactose. In particular cases, isotonic solutions such as phosphate buffered saline are used. The formulations can further encompass stabilizers such as gelatin and albumin. In some embodiments, a vaso-constrictive agent is added to the formulation. The pharmaceutical preparations according to the present invention are generally provided sterile and pyrogen-free. However, it is well known by those skilled in the art that the formulations for the pharmaceutically accepted carrier are those pharmaceutical carriers approved in the regulations promulgated by the United States Department of Agriculture, or equivalent government agency in a foreign country such as Canada or Mexico, or any one of the European nations, for any canine vaccine, polypeptide (antigen) subunit immunogenic compositions and vaccines, recombinant virus vector vaccines, and DNA vaccines. Therefore, the pharmaceutically accepted carrier for commercial production of the immunogenic compositions or vaccines is a carrier that is already approved or will be approved by the appropriate government agency in the United States of America or foreign country. The immunogenic compositions and vaccines can further be mixed with an adjuvant that is pharmaceutically acceptable. In certain formulations of the immunogenic compositions and vaccines, the immunogenic composition or vaccine is combined with other canine immunogenic compositions or vaccines to produce a polyvalent product that can protect canine against a wide variety of diseases caused by other canine pathogens.

Detection and Diagnostic Methods

The extent and nature of the immune responses induced in the animal can be assessed by using a variety of techniques. For example, sera can be collected from the inoculated animals, and tested for the presence or absence of antibodies specific for the immunogens. Detection of responding cytotoxic T-lymphocytes (CTLs) in lymphoid tissues, indicative of the induction of a cellular immune response, can be achieved by assays such as T cell proliferation. The relevant techniques are well described in the art.

Kits

Inasmuch as it may be desirable to administer an immunogenic composition or vaccine in combination with additional compositions or compounds—for example, for the purpose of treating a particular disease or condition—it is within the scope of the present invention that an immunogenic composition or vaccine can conveniently be included in, or combined in, the form of a kit suitable for administration or co-administration of the compositions.

Thus, kits encompassed by the present invention can comprise one or more separate pharmaceutical compositions, at least one of which is an immunogenic composition or vaccine in accordance with the present invention, and a means for separately retaining said compositions, such as a container, divided bottle, or divided foil packet. An example of such a kit is a syringe and needle, and the like. A kit of the present invention is particularly suitable for administering different dosage forms, for example, oral or parenteral, for administering the separate compositions at different dosage intervals, or for titrating the separate compositions against one another. To assist one administering a composition encompassed by the present invention, the kit typically comprises directions for administration.

Another kit encompassed by the present invention can comprise one or more reagents useful for the detection of an infected animal. The kit can include reagents for analyzing a sample for the presence of whole microorganisms, polypeptides, epitopes or polynucleotide sequences. The presence of virus, bacteria, polypeptides, or polynucleotide sequences can be determined using antibodies, PCR, hybridization, and other detection methods known to those of skill in the art.

Another kit encompassed by the present invention can provide reagents for the detection of antibodies against particular epitopes. Such reagents are useful for analyzing a sample for the presence of antibodies, and are readily known and available to one of ordinary skill in the art. The presence of antibodies can be determined using standard detection methods known to those of skill in the art.

In certain embodiments, the kits can include a set of printed instructions, or a label indicating that the kit is useful for the detection of infected animals.

Antibodies

Antibodies can either be monoclonal, polyclonal, or recombinant. The antibodies can be prepared against the immunogen or a portion thereof. For example, a synthetic peptide based on the amino acid sequence of the immunogen, or prepared recombinantly by cloning techniques, or the natural gene product and/or portions thereof can be isolated and used as the immunogen. Immunogens can be used to produce antibodies by standard antibody production technology well known to those skilled in the art. Antibody fragments can also be prepared from the antibodies by methods known to those skilled in the art, and include Fab, F(ab')$_2$, and Fv fragments.

In the production of antibodies, screening for the desired antibody can be accomplished by standard methods in immunology known in the art. In general, ELISAs and Western blotting are the preferred types of immunoassays. Both assays are well known to those skilled in the art. Both polyclonal and monoclonal antibodies can be used in the assays. The antibody can be bound to a solid support substrate, conjugated with a detectable moiety, or be both bound and conjugated as is well known in the art. The binding of antibodies to a solid support substrate is also well known in the art. The detectable moieties contemplated for use in the present invention can include, but are not limited to, fluorescent, metallic, enzymatic and radioactive markers such as biotin, gold, ferritin, alkaline phosphatase, b-galactosidase, peroxidase, urease, fluorescein, rhodamine, tritium, $^{14}$C, and iodination.

The present invention is further illustrated by, but by no means limited to, the following examples.

EXAMPLES

Example 1. Experimental Infection of Dogs with CRCV Using Intranasal Aerosolization Fifty dogs, determined to be in good general health, and negative to antibodies against canine respiratory coronavirus (CRCoV) prior to Day 0, as determined by indirect fluorescent antibody assay (IFA), were included in the study. Animals were also confirmed free from CRCoV as determined by oropharyngeal swab virus isolation on Day 0.

TABLE 1

Study Design

| | | Challenge | | | | |
|---|---|---|---|---|---|---|
| Group | N | Challenge Material | Method | Day | Target Dose | Necropsy Day |
| T01 | 5 | Saline | Aerosol-ization | 0 | NA | 4 |
| T02 | 5 | Saline | | | | 14 |
| T03 | 10 | CRCoV Max isolate | | | $10^{6.0}$TCID$_{50}$ | 4 |
| T04 | 10 | CRCoV Max isolate | | | | 14 |
| T05 | 10 | CRCoV NP787 isolate | | | | 4 |
| T06 | 10 | CRCoV NP787 isolate | | | | 14 |

NA = Not Applicable

The CRCoV isolate designated Max was used as the challenge material, and was obtained after a single passage on HRT18G cells. The challenge material was titrated on HRT18G cells, and determined to have an infectious dose of $10^{7.1}$ TCID$_{50}$/mL. The CRCoV isolate designated CRCoV NP787 was also used as the challenge material, and was obtained after two passages on HRT18G cells. The challenge material was titrated on HRT18G cells, and determined to have an infectious dose of $10^{6.5}$ TCID$_{50}$/mL.

Animals were observed once daily from arrival to Day −3. Body weights were determined on Day −1. A blood sample was collected from each animal on Day 0 prior to challenge. Tympanic temperatures were determined on Day −2, Day −1, and Day 0 prior to challenge. Two sets of oropharyngeal swabs were collected from each dog prior to challenge on Day 0. One set of swabs was collected into VTM (viral transport media) tubes for CRCoV virus isolation, and the other set was collected into Amies media (bacterial isolation). Two sets of nasal swabs were collected from each dog prior to challenge on Day 0, one into VTM tubes for CRCoV virus isolation, and the other into Amies media for bacterial isolation. Animals were observed once daily on Day −2, Day −1, and Day 0 prior to challenge, for clinical signs of respiratory disease.

CRCoV challenge virus stocks were thawed, and appropriately diluted to the expected challenge dose ($10^{6.0}$ TCID$_{50}$/dog). Five dogs were challenged at the same time, by aerosolizing the challenge containing 5×$10^{6.0}$ TCID$_{50}$ to target challenge dose of 1×10^6 TCID50 per dog. Challenge material was kept on ice until challenge inoculation. Dogs from treatment groups T01 and T02 were administered saline by aerosolization in a Plexiglass chamber for a total of 30 minutes on Day 0. These groups were challenged first to avoid cross-contamination. Dogs from treatment groups T03 and T04 were administered CRCoV Max isolate by aerosolization in a Plexiglass chamber for a total of 30 minutes on Day 0. Dogs from treatment groups T05 and T06 were administered CRCoV NP787 by aerosolization in a Plexiglass chamber for a total of 30 minutes on Day 0. Post-challenge titration average for CRCoV (Max) was $10^{5.2}$ $TCID_{50}$/mL, and post challenge titration average for CRCoV (NP787) was $10^{4.7}$ $TCID_{50}$/mL.

Tympanic temperatures were determined daily after challenge from Day 0 to Day 14. Clinical observations were performed once daily for approximately 30 minutes from Day 0 to Day 14. Nasal swabs were collected from each dog into VTM tubes for CRCoV virus isolation from Day 0 to Day 10. Oropharyngeal swabs were collected from each dog into VTM tubes on Day 2, Day 3 and Day 4. A blood sample for serology was collected from each animal on Day 4 and on Day 14.

Necropsy was performed on treatment groups T01, T03, and T05 on Day 4 post-challenge, and on treatment groups T02, T04, and T06 on Day 14 post-challenge. Animals were euthanatized with an overdose of sodium barbiturate. At necropsy, a complete lung was aseptically removed and placed on a sterile drape. To determine the total amount of lung consolidation, each lung lobe was scored for consolidation separately. The trachea was transected and the lumen evaluated for gross pathology. All tissues were evaluated and scored by a board-certified Veterinary Pathologist.

After the lungs had been scored, the right caudal lung lobe was lavaged by flushing approximately 30.0 mL VTM (without antibiotic or antimycotic) via the bronchial plexus. The VTM media was slowly aspirated back into the syringe while gently massaging the lung tissue. The lavaged fluids were aliquoted and tested for bacteriology, and for CRCoV virus isolation.

Tissue samples were collected from the trachea, nasal cavity (including the ciliated section), and right cranial lobe. Two sets of tissue samples were collected from the trachea and the nasal cavity. One set was tested for CRCoV virus isolation, and the other set prepared for histopathology. Three sets of tissue samples were collected from the right cranial lung lobe, the first set was tested for bacteriology, the second set was tested for CRCoV virus isolation, and the third set prepared for histopathology.

Nasal and oropharyngeal swabs, tissue samples, and lung lavages were tested for CRCoV virus isolation using HRT18G cells. Briefly, samples were processed and inoculated into flasks containing monolayers of HRT18G cells. Inoculated flasks were incubated for two weeks in a humidified $CO_2$ incubator at 35-37° C. Inoculated flasks were sampled at one and two weeks post-inoculation, as samples were inoculated into 4 wells of a 96-well plate seeded with HRT18G cells. Inoculated plates were incubated in a humidified $CO_2$ incubator for 5-7 days at 35-37° C. At the end of the incubation period, cell monolayers in the 96-well plates were fixed with an acetone-based solution, and washed with water. The presence was CRCoV was determined by fluorescent antibody staining using a CRCoV-specific FITC-conjugated antibody, and observed under an epifluorescent microscope.

Serum samples were tested for CRCoV antibodies by IFA. Briefly, HRT18G cells were seeded into 96-well plates, and infected with CRCoV with a virus dilution to achieve 50-200 infected cells per well. Infected plates were fixed with an acetone-based solution and rinsed. The test serum samples were diluted 2-fold directly into the CRCoV-fixed plates. Plates were incubated for 40-60 minutes. Plates were rinsed, and rabbit anti-canine IgG FITC-conjugated antibody was added. Plates were incubated for 40-60 minutes. After incubation, plates were rinsed and examined under an epifluorescent microscope. The antibody titer was determined as the reciprocal of the highest serum dilution exhibiting typical (+1) or more fluorescence intensity.

Serum samples were tested for CRCoV serum neutralizing antibodies by serum neutralization. Briefly, HRT18G cells were seeded into 96-well tissue culture plates at the appropriate density, and incubated for 3-5 days at 35-37° C. in a humidified $CO_2$ incubator. When cell monolayer reached 100% confluency, wells were rinsed with media and pre-treated with trypsin-supplemented media for 1 hour in the incubator. Two-fold dilutions of each test serum were prepared, and incubated with 50-300 $TCID_{50}$ CRCoV for 40-60 minutes at room temperature. Virus-serum mixtures from each serum dilution were inoculated into four wells. The plates were incubated for 5-7 days at 35-37° C. in a humidified $CO_2$ incubator. After incubation, media was discarded, and cell monolayers were fixed with an acetone-based solution. The fixative was discarded and plates were rinsed. The presence of CRCoV was determined by immunofluorescence, using a CRCoV-specific FITC-conjugated antibody, under an epifluorescene microscope. Serum neutralizing antibody titer was determined as the reciprocal of the highest serum dilution that neutralized virus in 50% of the wells.

The primary efficacy variables were the presence/absence of damaged tracheal ciliated epithelium scored with grade >1 (histopathology of the trachea), and virus isolation. No hypothesis tests were conducted. Frequency distributions of the histopathology scores (severity, distribution, process and cilia) of the trachea, nasal cavity, and cranial lung lobe, were calculated for each treatment group. In addition, the tracheal ciliated epithelium was further classified as normal (0 and 1) or abnormal (2, 3, and 4). Frequency distributions of this variable were calculated for each treatment. Frequency distributions of the presence or absence of CRCoV virus isolation from the nasal and oropharyngeal swabs were calculated for each treatment group and time point. The number of days that an animal had CRCoV virus detected in the nasal swabs post-challenge [(last day virus detected−first day virus detected)+1 unless no virus was detected] was calculated for each animal. The number of days with virus detected from the nasal swabs was summarized for each treatment, with descriptive statistics which included the mean, median, standard deviation, minimum and maximum. Frequency distributions of the presence/absence of virus isolation from lavage and tissue data were calculated for each treatment group. Descriptive statistics of antibody titers (IFA and SN), including the geometric mean, minimum and maximum, were calculated for each treatment and time point. Frequency distributions of each clinical observation (nasal discharge, coughing, sneezing ocular discharge, conjunctivitis, and depression) were calculated for each treatment group and time point. Descriptive statistics were calculated for temperature, including the mean, standard deviation, minimum and maximum for each treatment and time point. Additionally, temperatures were classified as <37.0° C., 37.0-39.5° C., 39.6-40.0° C., 40.1-41.0° C. and 41.1-42.0° C. Frequency distributions were calculated for each treatment and time of this new variable. Frequency distributions of presence/absence of each test were calculated for each treatment and time.

Results. All dogs tested negative for CRCoV virus isolation from nasal and oropharyngeal swab samples collected on Day 0 (prior to challenge administration). All dogs tested negative (<40 IFA titer) for CRCoV antibodies by indirect fluorescent assay, and negative (3 SN titer) for CRCoV antibodies by serum neutralization assay, from serum samples collected on Day 0 (prior to challenge administration). All dogs tested negative for *Bordetella bronchiseptica* and to *Pasteurella* sp from nasal and oropharyngeal swabs collected on Day 0, but *Mycoplasma* sp, *Staphylococcus intermedius* and *Streptococcus canis* were isolated from nasal and oropharyngeal swabs at different levels on Day 0. Healthy dogs frequently harbor these microorganisms as part of their normal flora in the upper respiratory tract, however.

The majority of the post-challenge clinical signs for the animals administered CRCoV Max isolate (treatment groups T03 and T04) and CRCoV NP787 isolate (treatment groups T05 and T06), were from mild to moderate, and included nasal discharge, coughing, sneezing and ocular discharge. Conjunctivitis was never observed, and a single dog presented depression. There appeared to be no major differences between the two challenge isolates (CRCoV Max and CRCoV NP787) associated with pathogenicity of the clinical signs observed for treatment groups T03 and T04 (challenged with CRCoV Max isolate), and for treatment groups T05 and T06 (challenged with CRCoV NP787 isolate).

Some dogs administered the placebo (saline) in treatment groups T01 and T02, presented mild and moderate ocular discharge during the challenge phase of the study. However, all of these dogs were already presenting mild ocular discharge prior to challenge Day 0. The post-challenge tympanic temperatures were normal (≤39.4° C.) for all the dogs challenged with the CRCoV Max isolate (treatment groups T03 and T04), and for all the dogs challenged with CRCoV N P787 isolate (treatment groups T05 and T06). Some dogs administered the placebo in treatment groups T01 and T02 presented hyperthermia (≥39.5° C.) at some point during the challenge phase of the study. However, all these dogs were perfectly normal and healthy, and it was later found that the tympanic thermometer used for treatment groups T01 and T02 was running high.

In summary, due to the mild intensity of CRCoV clinical signs, and due to the absence of hyperthermia in the challenge dogs (CRCoV Max isolate and CRCoV NP787 isolate), these two criteria do not appear to be sufficient to characterize and measure the intensity of the disease under laboratory conditions.

The mean number of days of CRCoV virus isolation from nasal swabs for treatment group T03 (CRCoV Max isolate, Necropsy Day 4) was 4, and for treatment group T04 (CRCoV Max isolate, Necropsy Day 14) was 6. The mean number of days of CRCoV virus isolation from nasal swabs for Treatment Group T05 (CRCoV NP787 isolate, Necropsy Day 4) was 2, and for treatment group T06 (CRCoV NP787 isolate, Necropsy Day 14) was 5. Four dogs administered the placebo (saline) from treatment group T02 were positive for CRCoV virus isolation from nasal swabs around Day 6, Day 7 and Day 8 post-challenge. None of these animals presented any clinical signs suggestive of CRCoV infection during the post-challenge phase. At necropsy, on Day 14 post-challenge, three dogs T02 had overall mild lung scores. Cilia assessment was considered normal for all these animals. No CRCoV isolation was obtained from lung, lung lavage, nasal cavity and trachea for all these animals, and for this reason, it is unlikely the wild-type CRCoV isolate was cross-contaminated into the placebo (saline) animal room. In addition, the positive CRCoV virus isolation results were only found at the second passage in HRT18G cells. One possibility is that the samples were cross-contaminated at the laboratory testing phase.

The mean number of days of CRCoV virus isolation from oropharyngeal swabs for treatment group T03 (CRCoV Max isolate, Necropsy Day 4) was 2, and for treatment group T04 (CRCoV Max isolate, Necropsy Day 14) was 2. The mean number of days of CRCoV virus from oropharyngeal swabs for treatment group T05 (CRCoV NP787 isolate, Necropsy Day 4) was 0, and for treatment group T06 (CRCoV NP787 isolate, Necropsy Day 14) was 1. The numerically highest mean days of CRCoV isolation were obtained from swabs collected from the nasal cavity using the CRCoV Max isolate as the challenge organism (treatment groups T03 and T04). In conclusion, nasal swabs collected during the earliest phase of infection appeared to be more likely to result in positive CRCoV virus isolation from dogs challenged with the CRCoV Max isolate.

No CRCoV virus isolation was observed from lung tissue collected from the placebo (saline) challenged dogs. Positive CRCoV virus isolation from lung tissue was observed in 10 out of 10 dogs (100%) at Necropsy Day 4 for treatment group T03 (CRCoV Max isolate). Positive CRCoV virus isolation from lung tissue was observed in 7 out of 10 dogs (70%) at Necropsy Day 4 for treatment group T05 (CRCoV NP787 isolate). No CRCoV virus isolation was obtained from lung tissue collected at necropsy on Day 14 for treatment group T04 (CRCoV Max isolate) or for treatment group T06 (CRCoV N P787 isolate).

No CRCoV virus isolation was observed from lung lavage collected from the placebo (saline) challenged dogs. Positive CRCoV virus isolation from lung lavage was observed in 10 out of 10 dogs (100%) at Necropsy Day 4 for treatment group T03 (CRCoV Max isolate) and treatment group T05 (CRCoV NP787 isolate). No CRCoV virus isolation was obtained from lung lavage collected at necropsy on Day 14 for treatment group T04 (CRCoV Max isolate) or treatment group T06 (CRCoV NP787 isolate).

No CRCoV virus isolation was observed from the nasal cavity collected from the placebo (saline) challenged dogs. Positive CRCoV virus isolation from the nasal cavity was observed in 10 out of 10 dogs (100%) at Necropsy Day 4 for treatment group T03 (CRCoV Max isolate) and treatment group T05 (CRCoV NP787 isolate). No CRCoV virus isolation was obtained from the nasal cavity collected at necropsy on Day 14 for treatment group T04 (CRCoV Max isolate) or treatment group T06 (CRCoV NP787 isolate).

No CRCoV virus isolation was observed from the trachea collected from the placebo (saline) challenged dogs. Positive CRCoV virus isolation from the trachea was observed in 10 out of 10 dogs (100%) at Necropsy Day 4 for treatment group T03 (CRCoV Max isolate) or treatment group T05 (CRCoV NP787 isolate). No CRCoV virus isolation was obtained from the trachea collected at necropsy on Day 14 for treatment group T04 (CRCoV Max isolate) and for treatment group T06 (CRCoV NP787 isolate).

Both challenge isolates (CRCoV Max and CRCoV NP787) were successfully isolated from lung, lung lavage, nasal cavity and trachea collected at necropsy Day 4. No CRCoV virus isolation was obtained from lung, lung lavage, nasal cavity and trachea collected at necropsy Day 14 for both challenge isolates (CRCoV Max and CRCoV NP787). In conclusion, lung, lung lavage, nasal cavity and trachea collected during the earliest phase of infection appeared to be more likely to result in positive CRCoV virus isolation.

No clinically significant pathological changes were observed in the ciliated epithelia of the lung tissue. The majority of the dogs in all treatment groups scored grade 0. A single dog in treatment group T03 (CRCoV Max isolate) at Necropsy Day 4 scored grade 1.

No clinically significant pathological changes were observed in the ciliated epithelia of the nasal cavity for treatment groups T01 and T02 (Saline) at Necropsy Days 4 and 14, respectively. For treatment group T03 (CRCoV Max isolate) at Necropsy Day 4, all 10 dogs displayed pathology grade 2 or higher. For treatment group T04 (CRCoV Max isolate) at Necropsy Day 14, 6 out of 10 dogs (60%) displayed pathology grade 2 or higher. For treatment group T05 (CRCoV N P787 isolate) at Necropsy Day 4, 9 out of 10 dogs (90%) displayed pathology grade 2 or higher. For treatment group T06 (CRCoV NP787 isolate) at Necropsy Day 14, 7 out of 10 dogs (70%) displayed pathology grade 2.

No clinically significant pathological changes were observed in the ciliated epithelia of the trachea for treatment groups T01 and T02 (Saline) at Necropsy Days 4 and 14, respectively. For treatment group T03 (CRCoV Max isolate) at Necropsy Day 4, 7 out of 10 dogs (70%) displayed pathology grade 2 or higher. For treatment group T04 (CRCoV Max isolate) at Necropsy Day 14, all 10 dogs (100%) displayed pathology grade 1. For treatment group T05 (CRCoV NP787 isolate) at Necropsy Day 4, all 10 dogs (100%) displayed pathology grade 2 or higher. For treatment group T06 (CRCoV NP787 isolate) at Necropsy Day 14, all 10 dogs (100%) displayed pathology grade 1. No grade 2 or higher pathological changes were observed in the lung of animals challenged with both challenge isolates (CRCoV Max and CRCoV NP787). Grade 2 or higher pathological changes in the ciliated epithelium of the nasal cavity and trachea were observed in animals challenged with both challenge isolates (CRCoV Max and CRCoV NP787). The majority of the pathological changes (grade 2 or higher) in the nasal cavity and in the trachea were observed at Necropsy Day 4. In conclusion, ciliated epithelium damage was observed in the nasal cavity and in the trachea of animals challenged with both isolates (CRCoV Max and CRCoV NP787) and these pathological findings appeared to be more pronounced during the earliest phase of infection (Necropsy Day 4).

The most prominent histopathological finding was multifocal inflammation of the lung, nasal cavity and trachea, at different grades.

All dogs tested negative (<40 IFA) for CRCoV antibodies by indirect fluorescent assay from serum samples collected on Day 4. All placebo (saline) challenge dogs tested negative (<40 IFA) for CRCoV antibodies by indirect fluorescent assay from serum samples collected on Day 14. Dogs in treatment group T04 (CRCoV Max isolate), at Necropsy Day 14, had 1040 geometric mean IFA antibody titers from serum samples collected. Dogs in treatment group T06 (CRCoV NP787 isolate0, at Necropsy Day 14, had 1689 geometric mean IFA antibody titers from serum samples collected.

All dogs tested negative (3 SN titer) for CRCoV neutralizing antibodies by serum neutralization assay from serum samples collected on Day 4. All placebo (saline) challenge dogs tested negative (3 SN titer) for CRCoV neutralizing antibodies by serum neutralization assay from serum samples collected on Day 14. Dogs in treatment group T04 (CRCoV Max isolate), at Necropsy Day 14, had 100 geometric mean SN antibody titers from serum samples collected. Dogs in treatment group T06 (CRCoV NP787 isolate), at Necropsy Day 14, had 34 geometric mean SN antibody titers from serum samples collected.

All dogs tested negative to *Bordetella bronchiseptica*, *Pasteurella* sp, *Staphylococcus intermedius* and *Streptococcus canis* from lung lavage and lung tissue collected on either Day 4 or Day 14 necropsies. *Mycoplasma* sp was isolated from lung lavage from 2 dogs administered the placebo saline (treatment groups T01 and T02). *Mycoplasma* sp was isolated from lung lavage from 3 dogs administered CRCoV Max isolate (treatment group T03). *Mycoplasma* sp was also isolated from lung tissue from 1 dog administered CRCoV Max isolate (treatment group T03). These dogs had no indication of bacterial pneumonia at necropsy. All dogs tested negative for CRCoV virus isolation from nasal and from oropharyngeal swabs collected on Day 0 (prior to challenge administration). All dogs tested negative for CRCoV antibodies (IFA and SN) from serum samples collected on Day 0 (prior to challenge administration). All dogs tested negative for *Bordetella bronchiseptica* from nasal and oropharyngeal swabs collected on Day 0 (prior to challenge administration). Thus, the inclusion criteria for the study were met.

Conclusions. All dogs challenged with CRCoV Max isolate tested positive for virus isolation from nasal swabs and oropharyngeal swabs during the post-challenge phase. All dogs challenged with CRCoV NP787 isolate tested positive for virus isolation from nasal swabs, and 40-50% of the dogs tested positive for virus isolation from oropharyngeal swabs during the post-challenge phase. Therefore, this study had a valid challenge.

All dogs challenged with CRCoV Max isolate tested positive for virus isolation from lung, lung lavage, nasal cavity and trachea at necropsy Day 4. All dogs challenged with CRCoV NP787 isolate tested positive for virus isolation from lung lavage, nasal cavity, trachea and 70% of the dogs tested positive for virus isolation from lung at necropsy Day 4. Once again, this confirms that this study had a valid challenge.

The majority of the post-challenge clinical signs for the animals administered CRCoV Max isolate (treatment groups T03 and T04) and CRCoV N P787 isolate (treatment groups T05 and T06) were from mild to moderate, and included nasal discharge, coughing, sneezing and ocular discharge. Conjunctivitis and hyperthermia ($\geq 39.5°$ C.) were never observed, and a single dog presented depression. Clinical signs and tympanic temperatures do not appear to be sufficient to characterize and to measure the intensity of the CRCoV-induced disease under laboratory conditions.

The numerically highest mean days of CRCoV isolation were obtained from swabs collected from the nasal cavity using the CRCoV Max isolate. Nasal swabs collected during the earliest phase of infection appeared to be more likely to result in positive CRCoV virus isolation.

Both challenge isolates (CRCoV Max and CRCoV N P787) were successfully isolated from lung, lung lavage, nasal cavity and trachea collected at Necropsy Day 4. No CRCoV virus isolation was obtained from lung, lung lavage, nasal cavity and trachea collected at necropsy Day 14 for both challenge isolates (CRCoV Max and CRCoV NP787). In conclusion, lung, lung lavage, nasal cavity and trachea samples collected during the earliest phase of infection appear more likely to result in positive CRCoV virus isolation.

No grade 2 or higher pathological changes were observed in the lung of animals challenged with both challenge isolates (CRCoV Max and CRCoV NP787). Grade 2 or higher pathological changes in the ciliated epithelium of the nasal cavity and trachea were observed in animals administered either challenge isolate (CRCoV Max and CRCoV NP787). The majority of the pathological changes (grade 2 or higher) in the nasal cavity and in the trachea were observed at Necropsy Day 4. In conclusion, ciliated epithelium damage was observed in the nasal cavity and in the trachea of animals challenged with the isolates (CRCoV Max and CRCoV NP787), and these pathological findings appeared to be more pronounced during the earliest phase of infection (Necropsy Day 4).

All dogs tested negative for *Bordetella bronchiseptica, Pasteurella* sp, *Staphylococcus intermedius* and *Streptococcus canis* from lung lavage and lung tissue collected either on Day 4 or on Day 14 necropsies. *Mycoplasma* sp was isolated from lungs (lavage or tissue) from 6 dogs; however, no bacterial pneumonia was observed at necropsy. Overall, CRCoV was the only pathogen isolated from the respiratory tract, and appears to be responsible for the observed clinical signs and histopathology.

In conclusion, CRCoV Max isolate or CRCoV NP787 isolate, administered by aerosolization, resulted in viral infection and viral replication in the natural host. CRCoV was isolated from nasal swabs, oropharyngeal swabs, lung, lung lavage, nasal cavity and trachea from challenged dogs. The majority of the clinical signs were mild, and not relevant to characterization of the disease. However, the damage in the ciliated epithelium of the trachea and nasal cavity appear to be consistent parameters used to characterize the disease under laboratory conditions. The CRCoV challenge model and challenge isolates are suitable for use in vaccine efficacy studies for the CRCoV fraction.

Example 2. Development of Canine Respiratory Coronavirus (CRCoV), *Bordetella bronchiseptica* Dual Infection Model Thirty dogs, all in good general health, were included in the study. All animals were negative for antibodies to CRCoV as determined by immunofluorescent antibody assay (IFA) at <40 IFA titer at pre-screening, and negative (3 SN titer) for serum neutralizing antibodies to CRCoV prior to CRCoV challenge (Day 0). All dogs were also negative for CRCoV isolation from nasal swabs prior to CRCoV challenge (Day 0). All animals were unvaccinated against *Bordetella*, and had low antibody titers (<16 MAT titer) to *Bordetella* as determined by the Micro Agglutination Test (MAT) prior to *Bordetella* challenge (Day 3). All were also free of *Bordetella*, as determined by bacterial nasal swab isolation test, prior to CRCoV challenge (Day 0).

TABLE 2

Study Design

| Treatment Group | Challenge | N | Target Dose/Dog | Study Day | Route |
|---|---|---|---|---|---|
| T01 | Saline | 10 | NA | 0 | intranasal |
| T02 | *Bordetella* (Bihr cat) (051397-85B-2) | 10 | $10^{9.0}$ CFU | 3 | aerosolization |
| T03 | CRCoV (Max p1) CM (NB120586-123) | 10 | $10^{6.0}$ TCID$_{50}$ | 0 | via chamber |
|  | *Bordetella* (Bihr cat) (051397-85B-2) |  | $10^{9.0}$ CFU | 3 |  |

The CRCoV isolate, designated Max, was used as the challenge material. The virus was propagated and titered on HRT-18G cells, and determined to have a titer of $10^{7.1}$ TCID$_{50}$/mL. The Bihr cat strain of *Bordetella bronchiseptica* was used as the challenge material.

Animals were observed at least once daily from arrival to Day −3. Blood samples were collected on Day 0 prior to CRCoV challenge administration, and on Day 3, prior to *Bordetella* challenge administration. Tympanic temperatures were determined on Day −2, Day −1, and on Day 0. Three types of nasal swabs were collected from each dog prior to challenge Day 0: one was collected in vial transport media (VTM) tubes for CRCoV virus isolation; the second collected in Amies medium for bacterial examination; and the third collected in Tryptose Phosphate Broth (TPB) for *Bordetella* isolation. An additional set was collected on Day 3 prior to *Bordetella* challenge administration, for *Bordetella* isolation. Dogs were observed twice daily on Day −2, on Day −1, and on Day 0 (prior to challenge administration), for clinical signs of respiratory disease to establish the baseline values.

On Day 0, dogs in treatment group T01 were administered sterile saline by aerosolization in a Plexiglas chamber for approximately 30 minutes. Also on Day 0, dogs in treatment group T03 were administered CRCoV by aerosolization in a Plexiglas chamber for approximately 30 minutes. On Day 3, dogs in treatment groups T02 and T03 were challenged with *Bordetella* by aerosolization in the Plexiglas chamber for 30 minutes.

Clinical observations (approximately 30 minutes) were performed once on Day 0, and then twice daily (approximately 30 minutes each session) from Day 1 to Day 23. On Day 3, observations were performed prior to and after *Bordetella* challenge. On Day 24, a single observation was performed. Tympanic temperatures were determined daily after CRCoV challenge, from Day 0 to Day 24. Two types of nasal swabs were collected from each dog after challenge administration: one was collected in VTM tubes for CRCoV virus isolation from Day 1 to Day 10; and the second collected in Tryptose Phosphate Broth (TPB) for *Bordetella* isolation, starting on Day 6, isolating twice a week for three weeks, and then on Day 24. Another set of swab samples was collected prior to necropsy on Day 24 in Amies medium, without charcoal, for bacterial examination. Blood samples (approximately 6 mL) for serology were collected in SST tubes on Day 3, prior to *Bordetella* challenge, and on Day 24.

Necropsy was performed on Day 24 post-challenge. Dogs were euthanized with an overdose of sodium barbiturate. At necropsy, a complete lung was aseptically removed and placed on a sterile drape. To determine the total amount of lung consolidation, each lung lobe was scored separately. The trachea was transected, and the lumen evaluated for gross pathology. All tissues were evaluated and scored by a board-certified veterinary pathologist. After the lungs had been scored, the right caudal lung lobe was lavaged by flushing approximately 30.0 mL VTM (without antibiotic or antimycotic) via the bronchial plexus. The VTM media was slowly aspirated back into the syringe while gently massaging the lung tissue. The lavaged fluids were aliquoted and tested for bacteriology, as well as for CRCoV virus isolation. Tissue samples were collected from the trachea, nasal cavity (including the ciliated section), and right cranial lobe. Two sets of tissue samples were collected from the trachea and the nasal cavity. One set was tested for CRCoV virus isolation, and the other set prepared for histopathology. Two sets of tissue samples were collected from the right cranial lung lobe. The first set was tested for bacteriology, and the second set was tested for CRCoV virus isolation. One set of tissue samples, collected from the left middle lung lobe, was prepared for histopathology.

Nasal swabs, for isolation of *Bordetella*, were collected on Day 0 prior to CRCoV challenge, on Day 3 prior to *Bordetella* challenge, starting on Day 6 and isolating twice a week for three weeks, and on Day 24. Two Calgiswab swabs were used per dog, one swab per each nostril. Blood for serology (CRCoV by IFA/SN, and *Bordetella* by MAT) was collected prior to CRCoV challenge (Day 0), prior to *Bordetella* challenge (Day 3), and at the end of the study (Day 24). Approximately 6 mL of blood was collected from each dog at each time point. Serum was separated from the whole blood, and decanted into two cryovials. Sterile Dacron swabs were used for nasal swab collection for virus isolation. Swabs were collected on Day 0, prior to CRCoV challenge, on Day 3, prior to *Bordetella* challenge, and from Day 1 through Day 10. A swab was gently inserted into each nostril (one swab per dog) and then placed into sterile collection tubes containing approximately 3 mL of Viral Transport Medium (VTM supplemented with antibiotics). Nasal swabs were collected from each dog on Day 0 (prior to challenge administration) and on Day 24 (prior to necropsy). Swabs were placed into Amies transport medium without charcoal.

For the *Bordetella* antibody assay, agglutinating antibodies to *Bordetella* were determined by the Particulate Antigen (Micro) Agglutination Test (MAT). Briefly, two-fold serial dilutions of test serum, known positive serum, negative serum were prepared using "v" bottom microtiter plate, using normal saline containing 0.05% tween 20 as the diluent. Serum samples were added as 50 µL per well. A 50 µL of *Bordetella* antigen was added to each well and mixed for 60 seconds on microtiter plate mixer. The plates were incubated at 37±2° C. for 2 hours and then for 20-48 hours at 2-8° C. The plates were read visually on a mirror stand. The titers were expressed as the reciprocal of highest dilution showing complete agglutination.

For the CRCoV indirect fluorescent antibody assay, serum samples were titrated for anti-CRCoV antibodies by IFA. Briefly, HRT-18G cells were seeded in 96-well plates and infected with an optimal amount of CRCoV, to obtain between 50-200 infected cells per well. Infected plates were fixed with acetone-based fixative, rinsed, and stored. The test serum samples were serially diluted 2-fold directly in the antigen-fixed plates, and incubated for 40-60 minutes. The test serum was discarded, plates were rinsed, and rabbit anti-canine IgG FA-conjugated was added and incubated for 40-60 minutes. The wells were then rinsed, and plates were examined for fluorescence under the microscope. The antibody titer was determined as the reciprocal of the highest serum dilution exhibiting typical (+1) or more intense fluorescence.

For the CRCoV serum neutralization assay, CRCoV serum neutralizing antibody titers were determined on HRT-18G cells. Briefly HRT-18G cell were seeded in 96-well tissue culture plates at the appropriate density and incubated in a $CO_2$ incubator at 36° C.±1 for 3-5 days. When cell monolayers in the wells were 100% confluent, wells were rinsed with medium, and pre-treated with trypsin-supplemented media for at least 1 hour in the incubator. Two-fold dilutions of each test serum were prepared, and incubated with 50-422 $TCID_{50}$ CRCoV for 40-60 minutes at room temperature. Virus-serum mixtures from each serum dilution were inoculated into two wells. The plates were incubated in a humidified $CO_2$ incubator (3-5% $CO_2$) at 35-37° C. for 5-7 days. When incubation was complete, the plates were fixed, stained with CRCoV specific-FITC conjugated antibody, and examined under an epifluorescent microscope. Serum neutralizing antibody titer was determined as the reciprocal of the highest serum dilution that neutralized virus in 50% of the wells.

For CRCoV isolation, nasal swabs, tissues, and lung lavage samples were assayed for the presence of CRCoV on HRT-18G cells. Briefly, samples were processed and inoculated into flasks seeded with HRT-18G cells. Nasal samples were inoculated in T-25 flasks. Tissue and lung lavage samples were inoculated in T-150 flasks. Inoculated flasks were incubated overnight in a $CO_2$ incubator at 36° C.±1. Then, fetal bovine serum (FBS) was added to each flask (80 µL per T-25 flask or 500 µL per T-150 flask). The flasks were incubated for approximately 7 days in a $CO_2$ incubator at 36° C.±1. Samples were then collected, and inoculated into HRT cells in 96-well plates. Four wells of the plate were inoculated with 120 µl/well and additional 4 wells were inoculated with 30 µL/well. The 96-well plates were incubated for 5 to 7 days in a $CO_2$ incubator at 36° C.±1, and then fixed with acetone-based fixative, and then stained with CRCoV FA stain (all wells). The presence of virus in the sample was declared when typical fluorescence (CRCoV FA-positive cells) was observed under the microscope.

For CRCoV challenge virus titration, the titer of the challenge material was determined on HRT-18G. Briefly, HRT-18G cells were seeded in 96-well tissue culture plates at the appropriate density, and incubated in a $CO_2$ incubator at 36° C.±1 for 3-5 days. When the cell monolayer was 100% confluent, wells were rinsed with medium, and pre-treated with trypsin-supplemented media for 1 hour in the $CO_2$ incubator. Ten-fold serially diluted test sample was inoculated into the wells in 6 replicates per dilution. Plates were incubated in a humidified $CO_2$ incubator (3-5% $CO_2$) for 5-7 days at 35-37° C. After incubation, the media was discarded, and cells were incubated for 20-40 minutes with acetone-based fixative at room temperature. The fixative was discarded, and the plates were rinsed twice with water. CRCoV FITC-conjugated antibody was added to the wells, and incubated for 40-60 minutes at room temperature. When incubation was complete, the wells were rinsed twice with water before the plates were observed under an epifluorescent microscope for the presence of CRCoV-infected cells. The 50% end-point for infectivity was calculated using Spearman-Karber method and the virus titer was expressed as $log_{10}$ $TCID_{50}$/mL.

Nasal swabs, lung tissue and lavage samples were evaluated for the presence of *Bordetella bronchiseptica*, *Mycoplasma* sp., *Streptococcus canis*, *Staphylococcus intermedius*, and *Pasteurella* sp. according to standard procedures.

Slides for nasal cavity, lung, and tracheal tissues were prepared, and evaluated for histopathological lesions by a board-certified pathologist.

The criteria for a valid test are that all animals in the study must be: (i) free of CRCoV by virus isolation on Day 0; (ii) seronegative to CRCoV on Day 0; (iii) free of *Bordetella* on Day 0 and 3 (prior to *Bordetella* challenge) by bacterial isolation from nasal swabs; and (iv) susceptible to *Bordetella* prior to challenge, as determined by the MAT antibody titer remaining ≤16 on Day 0.

Respiratory clinical signs, including cough, were the primary criteria used to judge the extent of the disease. Bacterial isolation was the supporting secondary variable.

Frequency distributions of clinical observations (nasal discharge, cough, sneeze, ocular discharge, retch, depression and respiration) were calculated for each time point and treatment. The number and percentage of observation periods post-challenge which an animal had a particular clinical sign (nasal discharge, cough, sneeze, ocular discharge, depression, retch and respiration), and the number of days post-challenge with a particular clinical sign (nasal discharge, cough, sneeze, ocular discharge, depression, retch and respiration), were calculated for each animal. Descriptive statistics for the percent time periods with clinical signs, and the duration of each clinical sign, including the mean, median, standard deviation, minimums and maximums, were calculated for each treatment. Animals were classified as having a fever ($\geq 39.5°$ C.) or not having a fever ($<39.5°$ C.) on each day. Frequency distributions of fever/no fever were calculated for each treatment and time point. Frequency distributions of the presence or absence of CRCoV isolation from nasal swabs were calculated for each treatment group and time point. The number of days that an animal had CRCoV detected in the nasal swabs post-challenge (first day virus detected through the last day virus detected) were calculated for each animal. Treatment means, medians, standard deviations, minimums and maximums were calculated. Frequency distributions of the presence/absence of virus isolation from lung lavage, lungs, nasal cavity and trachea were calculated for each treatment group. Frequency distributions of bacterial isolation (positive/negative) were calculated for each treatment and time point. It was also determined for each animal whether or not it ever had bacteria isolated post-challenge, and a frequency distribution of that was calculated for each treatment. Frequency distributions of each type of histopathology score for the trachea, nasal cavity, and left middle lung lobe, were calculated for each treatment group. In addition, the tracheal cilia assessment was further classified as normal/histologically not relevant (0 and 1), or abnormal/histologically relevant (2, 3, and 4), and frequency distributions of this were calculated for each treatment.

Diffuse, discrete and total lung involvement were calculated with the following equation:

Percent involvement=0.53[(0.35×right cranial lobe)+ (0.15×right middle lobe)+(0.40×right caudal lobe)+(0.10×accessory lobe)]+0.47[(0.30×left cranial lobe)+(0.25×left middle lobe)+(0.45×left caudal lobe)]

Descriptive statistics including the mean, median, standard deviation, minimum and maximum were calculated for each treatment and type of lung involvement. Frequency distributions of the presence of gross lesions, discoloration and increased secretions were calculated for each treatment group. Treatment geometric means, minimums and maximums of the antibody titers were calculated for each time point. Frequency distributions of the presence/absence of Bordetella were calculated for each treatment group and time point.

Results. All dogs tested negative (<40 IFA titer) for CRCoV antibodies by indirect fluorescent assay, and negative (3 SN titer) for CRCoV antibodies by serum neutralization assay from serum samples collected on Day 0 (prior to challenge). All dogs tested negative for CRCoV by virus isolation from nasal swab samples collected on Day 0 (prior to challenge). All dogs tested negative for *Bordetella* antibodies (<16) by microagglutination test from serum samples collected on Day −21 and on Day 0 (prior to challenge). All dogs tested negative for *Bordetella* and *Pasteurella* sp. from nasal swabs collected prior to challenge administration (Day 0). *Mycoplasma* sp., *Staphylococcus pseudintermedius* and *Streptococcus canis* were isolated from nasal swabs at different levels on Day 0. (These varied between 0-80%, with percentages for *S. pseudintermedius* being the highest, at 50-80%.) However, healthy dogs frequently harbor these microorganisms as part of their normal flora in the upper respiratory tract. Thus, the inclusion criteria were met.

Titrations conducted on CRCoV challenge samples collected during challenge confirmed that $10^{4.5}$ TCID$_{50}$ was aerosolized per dog in the chamber. Plate count performed at the start and the end of challenge inoculation confirmed that an average of $5 \times 10^8$ CFU Bordetella was aerosolized per dog in the chamber.

The post-challenge tympanic temperatures were normal ($\leq 39.4°$ C.) for all the treatment groups. Mean, standard deviation, median, minimum and maximum were calculated for each individual clinical sign (nasal discharge, cough, sneeze, ocular discharge, retch, depression and respiration) to determine if there was any difference between treatment group T02 (*Bordetella*) and treatment group T03 (CRCoV and *Bordetella*). There was an increase in the percent time periods with nasal discharge for the dogs in treatment group T03 (CRCoV and *Bordetella*, mean=38.3) compared to the dogs in treatment group T02 (*Bordetella*, mean=7.2). There was also an increase in the percent time periods with ocular discharge for the dogs in treatment group T03 (CRCoV and *Bordetella*, mean=25.1) compared to the dogs in treatment group T02 (*Bordetella*, mean=9.6).

All dogs in treatment group T01 (placebo, saline), treatment group T02 (*Bordetella*), and treatment group T03 (CRCoV and *Bordetella*) tested negative (<40 IFA titer) for CRCoV antibodies by indirect fluorescent assay, and negative (3 SN titer) for CRCoV antibodies by serum neutralization assay from serum samples collected on Day 3. All dogs in treatment group T01 (placebo, saline) and treatment group T02 (*Bordetella*) tested negative (<40 IFA titer) for CRCoV antibodies by indirect fluorescent assay, and negative (3 SN titer) for CRCoV antibodies by serum neutralization assay from serum samples collected on Day 24. All dogs in treatment group T03 (CRCoV and *Bordetella*) tested positive for CRCoV antibodies by indirect fluorescent assay (geometric mean IFA titer=3151.7), and positive for CRCoV antibodies by serum neutralization assay (geometric mean SN titer=361.8) from serum samples collected on Day 24.

All dogs in treatment group T01 (placebo, saline), treatment group T02 (*Bordetella*), and treatment group T03 (CRCoV and *Bordetella*) tested negative to *Bordetella* antibodies ($\leq 8$) by MAT from serum samples collected on Day 3. All dogs in treatment group T01 (Placebo, Saline) tested negative to *Bordetella* antibodies (8) by MAT from serum samples collected on Day 24. Most dogs (8 out of 10) in treatment group T02 (*Bordetella*), and all dogs in treatment group T03 (CRCoV and *Bordetella*), had *Bordetella* antibodies (16) by MAT (geometric mean MAT titer for T02 and T03=13.9) from serum samples collected on Day 24.

The mean number of days of CRCoV virus isolation from nasal swabs was 0 for treatment group T01 (placebo, saline), 0 for treatment group T02 (*Bordetella*), and 6 for treatment group T03 (CRCoV and *Bordetella*). CRCoV was not isolated from lung lavage, lung tissue, nasal cavity or trachea at necropsy on Day 24 from any of the treatment groups.

*Bordetella* was isolated from nasal swabs collected on Days 6, 9, 13, 16, 20, 23 and 24 from treatment group T02 (*Bordetella*) and treatment group T03 (CRCoV and *Bordetella*). All dogs in treatment group T01 (placebo, saline) tested negative for *Bordetella* isolation from lung lavage and lung tissue collected on Day 24. All dogs in treatment group T02 (*Bordetella*) and in treatment group T03 (CRCoV and *Bordetella*) tested positive for *Bordetella* from lung lavage and lung tissue collected on Day 24. *Mycoplasma* sp., *Staphylococcus pseudintermedius* and *Streptococcus canis* were isolated from nasal swabs at different levels on Day 24. All dogs in treatment group T01 (placebo, saline), treatment group T02 (*Bordetella*) and treatment group T03 (CRCoV and *Bordetella*) tested negative for *Pasteurella* sp. on Day 24. A single dog in treatment group T03 (CRCoV and *Bordetella*) had *Mycoplasma* sp. isolated from lung lavage. All dogs in treatment group T01 (placebo, saline), treatment group T02 (*Bordetella*), and treatment group T03 (CRCoV and *Bordetella*) tested negative for *Pasteurella* sp., *Staphylococcus pseudintermedius*, and *Streptococcus canis* from lung lavage and from lung tissue at necropsy on Day 24.

Animals challenged with CRCoV and *Bordetella* (treatment group T03) had a higher incidence and severity in macroscopic and microscopic pulmonary lesions than animals challenged only with *Bordetella* (treatment group T02) and saline (placebo) animals (treatment group T01). Microscopic tracheal and nasal lesions had similar prevalence and severity in treatment groups T02 and T03. The incidence and severity of pulmonary lesions observed in animals with double challenge suggested that infection with CRCoV predisposes dogs to develop pneumonia after infection with *Bordetella*. However, these data have to be correlated with bacterial and viral analyses as well as with presentation of clinical signs in infected animals.

Conclusions. The inclusion criteria were met, in that: (i) all dogs were healthy and did not receive any *Bordetella* vaccinations; (ii) all dogs were negative for antibodies to CRCoV (<40 IFA titer), and negative (3 SN titer) for serum neutralizing antibodies to CRCoV prior to challenge; (iii) all dogs were negative for CRCoV isolation from nasal swabs prior to challenge; and (iv) all dogs had low antibody titers (≤8 MAT titer) to *Bordetella*, and were free of *Bordetella* isolation from nasal swabs prior to challenge.

The challenges were considered satisfactory, since: (i) all dogs challenged with CRCoV were positive for CRCoV virus isolation from nasal swabs (Day 24); and (ii) all dogs challenged with *Bordetella* were positive for the isolation of the bacteria from nasal swabs (Day 9).

The post-challenge tympanic temperatures were normal (≤39.4° C.) for treatment groups T01 (placebo, saline), T02 (*Bordetella*) and T03 (CRCoV and *Bordetella*). Regarding to the clinical signs that were assessed during the post-challenge phase (nasal discharge, cough, sneeze, ocular discharge, retch, depression and respiration), increases were observed in the percent time periods with nasal discharge for the dogs in treatment group T03 (CRCoV and *Bordetella*, mean=38.3) compared to the dogs in treatment group T02 (*Bordetella*, mean=7.2), and in the percent time periods with ocular discharge for the dogs in treatment group T03 (CRCoV and *Bordetella*, mean=25.1) compared to dogs in treatment group T02 (*Bordetella*, mean=9.6). The other clinical signs (cough, sneeze, retch, depression and respiration) did not appear to be different when comparing treatment group T02 (*Bordetella*) to treatment group T03 (CRCoV and *Bordetella*).

All dogs in treatment groups T02 (*Bordetella*) and T03 (CRCoV and *Bordetella*) tested positive for *Bordetella* from lung lavages, and from lung tissue collected at the end of the study (Day 24). CRCoV was not isolated from treatment group T03 (CRCoV and *Bordetella*) lung lavages, lung tissue, nasal cavity or tracheal samples collected at the end of the study (Day 24). Previous in-house studies have demonstrated that CRCoV is more readily isolated from lung lavage and from lung tissue within the first week post-challenge. All dogs in treatment groups T01 (placebo, saline), T02 (*Bordetella*) and T03 (CRCoV and *Bordetella*) tested negative for *Pasteurella* sp., *Staphylococcus pseudintermedius, Mycoplasma* sp. (except for one dog from treatment group T03) and *Streptococcus canis* from lung lavage and from lung tissue collected at the end of the study (Day 24). Diffuse, discrete and total lung consolidation means were higher for the animals challenged with CRCoV and *Bordetella* (treatment group T03). The incidence and severity of pulmonary lesions observed in these animals suggest that infection with CRCoV predisposes dogs to develop pneumonia after infection with *Bordetella*.

Overall, the nasal/ocular discharge and necropsy data appear to indicate that pre-infection of dogs with CRCoV increases the incidence and severity of respiratory disease upon a secondary infection by *Bordetella*.

Example 3. Efficacy of a CRCoV Vaccine Against Dual Challenge with CRCoV and *Bordetella bronchiseptica*

Sixty dogs, all in good general health, were included in the study. All animals had not received any *Bordetella* vaccinations, and as determined by the Micro Agglutination Test (MAT), had low level antibodies (≤8 MAT titer) to *Bordetella bronchiseptica* prior to vaccination (Day 0). All animals were also free of *B. bronchiseptica*, as determined by a bacterial nasal swab isolation test prior to vaccination (Day 0). All dogs were also negative for antibodies against CRCoV as determined by immunofluorescent antibody assay (IFA) at <40 IFA titer, as well as determined by serum neutralization (SN titer≤11) prior to vaccination on Day 0. All dogs were confirmed free from CRCoV by nasal swab virus isolation prior to vaccination on Day 0.

TABLE 3

Study Design

| | | | Vaccination | | | Challenge | |
| | | | Volume | Study | | Study | Target Dose/Dog |
| Group | IVP/CP[1] | N | (mL) | Days | Route | Days | CRCoV | *Bordetella* |
|---|---|---|---|---|---|---|---|---|
| T01 | Saline | 10 | 1.0 | 0, 21 | SC[2] | 42, 45 | 10^6 | 10^3 |
| T02 | CRCoV Vaccine | 10 | | | | | | |
| T03 | Saline | 10 | | | | | 10^6 | 10^5 |
| T04 | CRCoV Vaccine | 9 | | | | | | |
| T05 | Saline | 10 | | | | | 10^6 | 10^7 |
| T06 | CRCoV Vaccine | 10 | | | | | | |

[1]Investigational Veterinary Product (IVP) or Control Product (CP)—referred together as IVP.
[2]Subcutaneously The CRCoV isolate, designated Max, was used as the challenge material in this study. The virus stock was produced at first passage in HRT-18G cell line with a titer of $10^{7.1}$ TCID$_{50}$/mL. The *Bordetella bronchiseptica* Bihr cat strain was also used as the challenge material in this study.

Animals were observed for general health once daily, from arrival until challenge (Days −7 to 42). On vaccination days (Days 0 and 21), animals were observed twice (prior to and following vaccination). Blood samples for serology were collected from all animals on study on Days 0 and 21 (prior to vaccination), Day 42 (prior to challenge) and Day 65. Three types of nasal swabs were collected from each dog. Nasal swabs were collected in Virus Transport Medium (VTM) tubes for CRCoV virus isolation on Day 0, prior to vaccination, Day 42, prior to challenge, and once daily from Days 43 to 52. Nasal swabs were collected in tubes containing Tryptose Phosphate Broth (TPB) for *Bordetella* isolation. The swabs were collected on Day 0 prior to vaccination, Day 45 prior to challenge, and two times weekly for 3 weeks following challenge, and on Day 65. Nasal swabs were collected in Amies medium without charcoal, for bacteriology examination prior to challenge on Day 42. Tympanic temperatures were collected starting on Day −1; prior to and 3-6 hours after vaccination on Days 0 and 21, Days 1 to 7, and Days 22 to 28. Tympanic temperatures were collected once daily from Days 40 to 65. On challenge days (Day 42 and 45), two collections were made, pre-challenge and 3-6 hours after challenge.

Animals were palpated on the appropriate shoulder region on Day 0 and 21 prior to vaccination, to ensure that there were no pre-existing lesions on the injection site areas. Animals were administered the appropriate vaccine on Days 0 and 21, according to the study design shown in Table 3. The vaccines were administered subcutaneously to each dog in the right shoulder region for the first vaccination, and in the left shoulder region for the second vaccination. Potency of the CRCoV vaccine was determined by the ELISA test prior to vaccination. Animals were observed approximately 5 hours post vaccination on Days 0 and 21, and once daily on Days 1 to 7 and 22 to 28. On Day 42, CRCoV challenge virus stocks were thawed, and appropriately diluted to prepare a viral suspension to deliver a target challenge dose of $1\times10^6$ per dog. Challenge materials were kept on ice until challenge inoculation. On Day 45, *B. bronchiseptica* Bihr cat strain stock was used to prepare challenge material. At the final step of challenge suspension preparation, the organism concentration was adjusted to provide a target challenge dose of $10^3$ CFU per dog (T01/T02), $10^5$ CFU per dog (T03/T04), and $10^7$ CFU per dog (T05/T06). Challenge materials were kept on ice until challenge inoculation.

On Day 42, dogs from all treatment groups were administered the virus by aerosolization in a plexiglass chamber. On Day 45, dogs from the appropriate treatment groups were challenged with the assigned level of *B. bronchiseptica*, by aerosolization in a plexiglass chamber. For the T04 challenge group, one animal was removed from study prior to challenge.

Animals were observed twice daily (a.m. and p.m.), for approximately 30 minutes each session, on Days 40, 41, and 42, prior to challenge, for clinical signs of respiratory disease. Clinical observations were performed twice daily (a.m. and p.m.), approximately 30 minutes each session, from Day 42 and until Day 64. On Days 42 and 45, observations occurred prior to challenge, and 3-6 hours post-challenge administration. On Day 65, only one observation (a.m.) was performed. Necropsy was performed on all animals on Day 65 as part of the study evaluation. At necropsy, a complete lung was aseptically removed and placed on a sterile drape. The lung lobes were evaluated grossly, and an estimation of the percentage of volume of lung affected was assessed. Tissue evaluation was performed by an ACVP board-certified pathologist. To determine the percentage of volume of lung affected, each lung lobe was scored for percentage of tissue affected by gross changes, which may include, but are not limited to, discoloration (change in color), failure to collapse, or change in texture (firm/consolidated, elastic/rubbery, hard, or crepitus). Percentages of involvement by discrete or diffuse lesions were estimated. The trachea was transected, and the lumen evaluated for gross pathology. Two types of tissue samples (sections) were collected from the trachea and the nasal cavity—one for virus isolation, and another section for histopathology. The right cranial lung lobe was divided into two sections, one for virus isolation and one for a bacteriology sample. The whole left middle lung lobe was aseptically severed at the bronchial plexus and collected for histopathology. After all other samples (virus isolation and bacteriology) had been collected; the lobe was inflated with approximately 20-30 mL of 10% buffered formalin prior to being placed into a container of formalin.

Serum samples were titrated for CRCoV-specific antibodies by IFA for animal screening, and by serum neutralization (SN) for all other samples (Days 0, 21, 42, and 65), according to standard procedures.

Screening serum samples were titrated for CRCoV antibodies by IFA. Briefly, HRT-18G cells were seeded in 96-well plates, and infected with an optimal amount of CRCoV to obtain between 50-200 infected cells per well. Infected plates were fixed with acetone-based fixative, rinsed, and stored. The test serum samples were 2-fold serially diluted directly in the antigen-fixed plates, and incubated for 40-60 minutes. The test serum was discarded, plates were rinsed, and rabbit anti-canine IgG FA-conjugated was added and incubated for 40-60 minutes. The wells were then rinsed, and plates were examined for fluorescence under the microscope. The antibody titer was determined as the reciprocal of the highest serum dilution exhibiting typical (+1) or more intense fluorescence.

CRCoV serum-neutralizing antibody titers were determined on HRT-18G cells. Briefly HRT-18G cell were seeded in 96-well tissue culture plates at the appropriate density and incubated in a $CO_2$ incubator at 36° C.±1 for 3-5 days. When cell monolayers in the wells were 100% confluent, wells were rinsed with medium and pre-treated with trypsin-supplemented media for at least 1 hour in the incubator. Two-fold dilutions of each test serum were prepared and incubated with 50-422 $TCID_{50}$ CRCoV for 40-60 minutes at room temperature. Virus-serum mixtures from each serum dilution were inoculated into two wells. The plates were incubated in a humidified $CO_2$ incubator (3-5% $CO_2$) at 35-37° C. for 5-7 days. When incubation was complete, the plates were fixed, stained with CRCoV specific-FITC conjugated antibody, and examined under an epifluorescent microscope. Serum neutralizing antibody titer was determined as the reciprocal of the highest serum dilution that neutralized virus in 50% of the wells. Agglutinating antibodies to *B. bronchiseptica* were determined by the Particulate Antigen (Micro) Agglutination Test (MAT), according to standard procedure. Briefly, two-fold serial dilutions of test serum, known positive serum and negative serum were made in v-bottom microtiter plates, using normal saline containing 0.05% Tween 20 as the diluent. Serum samples were added at 50 μL per well. A 50 μL volume of *B. bronchiseptica* antigen was added to each well, and mixed for 60 seconds on a microtiter plate mixer. The plates were incubated at 37±2° C. for 2 hours, and then the plates were stored for 20-48 hours at 2-8° C. The plates were read visually on a mirror stand. The titer is expressed as the reciprocal of the highest dilution showing complete agglutination. Nasal swabs and tissues were assayed for the presence of CRCoV on HRT-18G cells. Briefly, samples were processed, and inoculated into flasks seeded with HRT-18G cells. Nasal samples were inoculated in T-25 flasks. Tissue and lung lavage samples were inoculated in T-150 flasks. Inoculated flasks were incubated overnight in a $CO_2$ incubator at 36° C.±1. Then, fetal bovine serum (FBS) was added to each flask (80 μL per T-25 flask or 500 μL per T-150 flask). The flasks were incubated for approximately 7 days in a $CO_2$ incubator at 36° C.±1. Samples were then taken and inoculated into HRT cells in 96-well plates. Four wells of the plate were inoculated with 120 μl/well, and an additional 4 wells were inoculated with 30 μL/well. The 96-well plates were incubated for 5 to 7 days in a $CO_2$ incubator at 36° C.±1, fixed with an acetone-based fixative, and then stained with CRCoV FA stain (all wells). The presence of virus in the sample was declared when typical fluorescence (CRCoV FA positive cells) was observed under the microscope.

The titer of the challenge material was determined on HRT-18G. Briefly, HRT-18G cells were seeded in 96-well tissue culture plates at the appropriate density, and incubated in a $CO_2$ incubator at 36° C.±1 for 3-5 days. When the cell monolayer was 100% confluent, wells were rinsed with medium, and pre-treated with trypsin-supplemented media for 1 hour in the $CO_2$ incubator. Ten-fold serially diluted test sample was inoculated into the wells, in 6 replicates per dilution. Plates were incubated a humidified $CO_2$ incubator (3-5% $CO_2$) for 5-7 days at 35-37° C. After incubation, the media was discarded, and cells were incubated for 20-40 minutes with acetone-based fixative at room temperature. The fixative was discarded, and the plates were rinsed twice with water. CRCoV FITC-conjugated antibody was added to the wells, and incubated for 40-60 minutes at room temperature. When incubation was complete, the wells were rinsed twice with water before the plates were observed under an epifluorescent microscope for the presence of CRCoV-infected cells. The 50% end-point for infectivity was calculated using Spearman-Karber method, and the virus titer was expressed as $\log_{10}$ $TCID_{50}$/mL.

Bordetella bronchiseptica isolation from nasal swabs was performed according to standard procedures. Each sample was tested qualitatively (presence or absence) for B. bronchiseptica. Nasal swabs and lung tissue samples were evaluated for the presence of B. bronchiseptica, Mycoplasma sp., Streptococcus canis, Staphylococcus intermedius, and Pasteurella sp. according to standard procedures. Slides for nasal cavity, lung, and tracheal tissues were prepared, and evaluated for histopathological lesions by an ACVP board-certified pathologist.

The percentage of observation periods post-challenge which an animal coughs and had nasal discharge, as well as the duration of days post-challenge with cough and nasal discharge, were calculated for each animal. Arcsine square root transformed percentage of observation periods and duration were analyzed with a general linear mixed model separately for each challenge dose (T01 vs T02, T03 vs T04, and T05 vs T06). The fixed effect in the model was treatment, and the random effects were block and residual. In addition to the least squares means, standard errors, and 90% confidence limits, the treatment minimums and maximums were calculated. The least squares means, standard errors and confidence limits were back-transformed as appropriate. Frequency distributions of the presence or absence of CRCoV virus isolation from the nasal swabs were calculated for each treatment group and time point. The number of days that an animal has CRCoV virus detected in the nasal swabs post-challenge (first day virus detected through the last day virus detected) was calculated for each animal. Frequency distributions of the presence/absence of virus isolation from tissue data were calculated for each treatment group. Frequency distributions of B. bronchiseptica isolation from swabs were calculated for each treatment. Frequency distributions of B. bronchiseptica isolation from nasal swabs were calculated for each treatment and time point. The number of days that an animal has bacteria detected in the nasal swabs post-challenge (first day virus detected through the last day virus detected) was calculated for each animal. Descriptive statistics of number of days including the mean, standard deviation, minimum and maximum were calculated for each treatment. Frequency distributions of clinical observations (sneeze, ocular discharge, retch, depression and respiration) were calculated for each time point and treatment. Animals were classified as having a fever (≥39.5° C.) or not having a fever (<39.5° C.) on each day. Frequency distributions of fever/no fever was calculated for each treatment and time point.

Diffuse, discrete and total lung involvement were calculated with the following equation:

Percent involvement=0.53((0.35×right cranial lobe)+ (0.15×right middle lobe)+(0.40×right caudal lobe)+(0.10×accessory lobe))+0.47((0.30×left cranial lobe)+(0.25×left middle lobe)+(0.45×left caudal lobe)).

Arcsine square root transformed percentage involvement was analyzed with a general linear mixed model separately for each challenge dose (T01 vs T02, T03 vs T04, and T05 vs T06). The fixed effect in the model was treatment, and the random effects were block and residual. In addition to the least squares means, standard errors, and 90% confidence limits, the treatment minimums and maximums were also calculated. The least squares means, standard errors and confidence limits were back-transformed. Frequency distributions of presence of gross lesions, discoloration and increased secretions were calculated for each treatment group. Frequency distributions of injection site observations (swelling and pain) were calculated for each time point and treatment. Descriptive statistics, including the geometric mean, minimum and maximum of the antibody titers, will be calculated for each treatment group and time point.

Results. There was no pain or fever (≥39.5° C.) reported in any of the dogs following vaccination.

The majority of vaccinates (T02,T04,T06) were reported to have scratching at the time of vaccination. Injection swellings were reported in most of the vaccinates, but these swellings resolved for the majority of dogs in 3 days or less. Three dogs were reported with hypersensitivity reactions during the 3-6 hours after the $2^{nd}$ vaccination observation. Two of the dogs were treated with Diphenhydramine to reverse the symptoms.

The CRCoV vaccine induced serum-neutralizing antibody responses in the vaccinated dogs after the first dose, indicating active immunization. The geometric mean serum neutralization (SN) response increased after the second vaccination to a GMT≥955 in the vaccinated groups (T02, T04,T06) compared to <4 in the saline control groups (T01, T03, T04), indicating booster effect of the vaccine. A robust anamnestic SN response (GMT≥11146) was achieved in the vaccinates when compared to the saline controls (GMT≤446) after challenge (Day 65), indicating effective immune memory response.

The efficacy of the CRCoV vaccine was evaluated against a dual challenge dose titration. The CRCoV challenge dose level (confirmed at $10^{5.5}$ $TCID_{50}$/dog) was kept constant, while the B. bronchiseptica challenge dose was given at a low target of $10^3$ CFU per dog (confirmed at 5.4×$10^3$) for groups T01 and T02, a medium target $10^5$ (confirmed at 4.2×$10^5$) for groups T03 and T04, and a high target $10^7$ (confirmed 4.3×$10^7$) for groups T05 and T06, to ensure the induction of optimum clinical disease. The post-challenge CRCoV and Bordetella organism isolation data indicated that infection was achieved in inoculated dogs at the three dose levels. However, based on the level of clinical disease induced in the dogs, as discussed below, the lower Bordetella challenge dose was determined as the optimum dose for evaluating vaccine efficacy. The saline-control dogs (T01, T03, and T05) displayed a wide range of respiratory clinical signs, including cough. The vaccinates (T02) had significant reduction in the duration and percent periods with cough (p-values 0.0470 and 0.0033, respectively), when compared with the controls (T01) in the low dose challenge group. The least square (LS) means for the duration and back-transformed LS means for percent period with cough in the control group (T01) were 10.8 and 14.7, compared to 5.3 and 2.4 in the vaccinates (T02), respectively. The reduction in cough diminishes between vaccinates and controls as the challenge dose is increased, likely due to over-challenge. The cough data clearly indicate that the CRCoV vaccine was able to induce immunity sufficient to reduce the cough induced by the dual challenge in the optimum challenge dose group. Nasal discharge data showed that the vaccinates (T02) had significantly reduced percent period with nasal discharge (mean 4.6) when compared to the controls (mean 17.4), with p-value 0.0299 in the low dose challenge group. As discussed for the cough, the reduction in nasal discharge between vaccinates and controls diminishes as an overchallenge dose is reached. The nasal discharge data clearly indicate efficacy of the vaccine against nasal discharge in the optimum challenge dose group. A total of 5 dogs were reported to have temperatures of ≥39.5° C. for one day each during the post-challenge period—four from the saline control groups, and one from a vaccinate group (T02; Day 44). While the data show less animals with fever in the vaccinates compared to the controls at the low dose, fever is not known as a consistent criterion for CRCoV, Bordetella or the dual challenge. Therefore, it was not used to judge the vaccine efficacy.

Gross necropsy evaluation of the respiratory organs was performed by an ACVP board-certified pathologist on Day 65. The examination revealed that the main necropsy finding was the lung consolidation. This is consistent with previous dual challenge study findings. Therefore, the lung consolidation was used as a criterion to judge vaccine efficacy. Significant reduction of discrete (mean percent 0.9 vs. 4.02), and total (mean percent 1.44 vs. 7.7) lung consolidation was observed in the vaccinates, when compared to the controls at the low dose challenge group, p-values 0.0457, and 0.093, respectively. Consistent with the clinical signs, the reduction effected by the vaccine diminishes as the challenge dose is increased, and an overchallenge is reached. It is important to note that there was no involvement by other respiratory pathogens in the lung tissues, as confirmed by the bacteriological examination results, i.e. the lung lesions reported were specifically the results of the dual challenge. The data suggest that prior infection with the virus predisposes the dogs by impacting their innate immune defenses, leading to more invasive bacterial infection. A typical pattern of virus-bacteria infection that occurs frequently in the field leading to the development of pneumonia in dogs in canine respiratory disease complex (CIRD), or in cattle in bovine respiratory disease complex (BRDC), and possibly also in other animal species. The data obtained in this study indicate that the vaccine was able to protect dogs by reducing the occurrence of bronchopneumonia caused by the dual challenge in vaccinated dogs, when compared to the controls at the optimum challenge dose.

Based on macroscopic and microscopic pathological analyses, the vaccination with CRCoV clearly protected dogs by reducing the incidence and severity of bronchopneumonia caused by controlled double intranasal challenge with $10^3$ CFU of B. bronchiseptica and $10^6$ TCID$_{50}$ of CRCoV. The protective effect is reduced when the challenge dose with B. bronchiseptica is increased at $10^5$ CFU or higher, perhaps due to the overwhelming of the innate and adaptive immune response. Furthermore, the pathological findings correlated well with the reduction in respiratory clinical signs reported in the vaccinated dogs.

There was no virus isolated from the tissues on Day 65 (23 days after CRCoV challenge) as expected, due to the quick hit-and run nature of the viral infection. The vaccine protected dogs by reducing the duration of nasal shedding in the vaccinates (T02) when compared to the saline controls (T01), indicating the ability of the vaccine to reduce infection in the optimum challenge dose group.

In summary, the clinical signs (cough, nasal discharge) and lung lesions (consolidation, histopathology) data obtained from this study unequivocally demonstrate protection afforded from the monovalent CRCoV vaccine against a dual CRCoV-B. bronchiseptica challenge. These data collectively indicate that the monovalent CRCoV vaccine was able to induce protective immunity in the vaccinated dogs that resulted in reduction of respiratory disease (cough, nasal discharge) and pneumonia (lung consolidation) caused by a dual CRCoV-B. bronchiseptica challenge. Therefore, the data provides proof of the utility of a CRCoV vaccine in reducing respiratory disease in dogs following an initial CRCoV infection, and subsequent bacterial infection.

We claim:

1. A method of treating a respiratory infection in a dog in need thereof, comprising administering to the dog in need thereof a composition comprising an antigenic component, the antigenic component consisting of canine respiratory coronavirus (CRCoV) and one or more of canine parainfluenza virus (CPIV), canine influenza virus (CIV), canine distemper virus (CDV), canine parvovirus (CPV), enteric canine coronavirus (CCV), canine adenovirus, Leptospira canicola, Leptospira grippotyphosa, Leptospira icterohaemorrhagiae, Leptospira pomona, Leptospira bratislava, canine herpesvirus, canine pneumovirus, Leishmania organisms, a Borrelia species, Mycoplasma species, rabies, and Ehrlichia canis and wherein further said respiratory infection is Canine Infectious Respiratory Disease (CIRD) caused by co-infection with CRCoV and B. bronchiseptica.

2. The method of claim 1, wherein the composition further comprises a pharmaceutically acceptable carrier, diluent or excipient.

3. A method of treating a respiratory infection in a dog in need thereof, comprising administering to the dog in need thereof a composition comprising an antigenic component, wherein the antigenic component consists of CRCoV, and wherein further said respiratory infection is CIRD caused by co-infection with CRCoV and B. bronchiseptica.

4. The method of claim 3, wherein the composition has a duration of efficacy against said Bordetella bronchiseptica infection for a period of at least 6 months.

5. The method of claim 1, wherein the antigenic component consists of canine respiratory coronavirus (CRCoV) and one or more of CIV, and CPIV.

6. The method of claim 1, wherein the composition has a duration of efficacy against said Bordetella bronchiseptica infection for a period of at least 6 months.

* * * * *